US010113169B2

(12) United States Patent
Rothman et al.

(10) Patent No.: US 10,113,169 B2
(45) Date of Patent: Oct. 30, 2018

(54) METHODS AND COMPOSITIONS FOR TREATING CANCER USING PEPTIDE NUCLEIC ACID-BASED AGENTS

(71) Applicant: Memorial Sloan-Kettering Cancer Center, New York, NY (US)

(72) Inventors: Jeffrey H. Rothman, Greenwich, CT (US); Gary K. Schwartz, Briarcliff Manor, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 15/104,701

(22) PCT Filed: Dec. 17, 2014

(86) PCT No.: PCT/US2014/070970
§ 371 (c)(1),
(2) Date: Jun. 15, 2016

(87) PCT Pub. No.: WO2015/100113
PCT Pub. Date: Jul. 2, 2015

(65) Prior Publication Data
US 2016/0319284 A1 Nov. 3, 2016

Related U.S. Application Data

(60) Provisional application No. 61/920,289, filed on Dec. 23, 2013.

(51) Int. Cl.
*C12N 15/113* (2010.01)
*C07K 14/00* (2006.01)
*C12Q 1/6886* (2018.01)
*G01N 33/574* (2006.01)
*A61K 38/00* (2006.01)

(52) U.S. Cl.
CPC ........ *C12N 15/1135* (2013.01); *C07K 14/003* (2013.01); *C12Q 1/6886* (2013.01); *G01N 33/5748* (2013.01); *A61K 38/00* (2013.01); *C12N 2310/3181* (2013.01); *C12N 2310/3513* (2013.01); *C12N 2310/3515* (2013.01); *C12N 2310/531* (2013.01); *C12N 2320/30* (2013.01); *C12Q 2600/136* (2013.01); *C12Q 2600/158* (2013.01); *G01N 2500/10* (2013.01)

(58) Field of Classification Search
CPC .............. C07K 14/003; C12N 15/1135; C12N 2310/3181; C12N 2310/3513; C12N 2310/3515
See application file for complete search history.

(56) References Cited

FOREIGN PATENT DOCUMENTS

WO WO 2008/043366 A2 * 4/2008

OTHER PUBLICATIONS

Maier et al. "Evaluation of Basic Amphipathic Peptides for Cellular Delivery of Antisense Peptide Nucleic Acids," J. Med. Chem. 2006, 49, 2534-2542.*
Zhang et al. ("Strand invasion by mixed base PNAs and a PNA-peptide chimera," Nucleic Acids Research, 2000, vol. 28, No. 17, pp. 3332-3338).*
Hu et al. ("Inhibiting Gene Expression with Peptide Nucleic Acid (PNA)-Peptide Conjugates That Target Chromosomal DNA," Biochemistry, 2007, vol. 46, pp. 7581-7589).*
Tran et al. ("Targeting V600EB-Raf and Akt3 Using Nanoliposomal-Small Interfering RNA Inhibits Cutaneous Melanocytic Lesion Development," Cancer Research, 2008, vol. 68, No. 18, pp. 7638-7649).*
Oikawa et al. ("A novel oncogenic pathway by TLS-CHOP involving repression of MDA-7/IL-24 expression," British Journal of Cancer, 2012, vol. 106, pp. 1976-1979).*
Fabani et al. ("Efficient inhibition of miR-155 function in vivo by peptide nucleic acids," Nucleic Acids Research, 2010, vol. 38, No. 13, pp. 4466-4475) (Year: 2010).*
Kaihatsu, K. et al., Extending recognition by peptide nucleic acids (PNAs): binding to duplex DNA and inhibition of transcription by tail-clamp PNA-peptide conjugates, Biochemistry, 42(47):13996-4003 (2003).
International Search Report for PCT/US2014/070970, 5 pages (dated Jun. 25, 2015).
Kaihatsu, K. et al., Extending recognition by peptide nucleic acids (PNAs): binding to duplex DNA and inhibition of transcription by tail-clamp PNA-peptide conjugates, Biochemistry, 42(47):13996-14003 (2003).
Shen, G. et al., Phospholipid conjugate for intracellular delivery of peptide nucleic acids, Bioconjug. Chem., 20(9):1729-36 (2009).
Torres, AG. et al., Chemical structure requirements and cellular targeting of microRNA-122 by peptide nucleic acids anti-miRs, Nucleic Acids Res., 40(5):2152-67 (2012).
Written Opinion for PCT/US2014/070970, 6 pages (dated Jun. 25, 2015).

* cited by examiner

Primary Examiner — Christina Bradley
(74) Attorney, Agent, or Firm — Bryan Cave Leighton Paisner LLP

(57) ABSTRACT

The present invention provides compositions and methods for treating cancer with peptide nucleic acid agents. In some embodiments, the present invention provides methods and compositions relating to peptide nucleic acid agents that target oncogenes. For example, the present invention provides compositions, including pharmaceutical compositions, comprising agents specific for BRAF V600E inhibition, or fragments or characteristic portions thereof. The present invention further provides various therapeutic and/or diagnostic methods of using BRAF V600E specific peptide nucleic acid agents and/or compositions.

13 Claims, 14 Drawing Sheets

Specification includes a Sequence Listing.

SEQUENCE LISTING

<160> NUMBER OF SEQ ID NOS: 4

<210> SEQ ID NO 1
<211> LENGTH: 3
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term AcNH
<220> FEATURE:
<221> NAME/KEY: MOD_RES
<222> LOCATION: (1)..(1)
<223> OTHER INFORMATION: Lys(palmitoyl)
<220> FEATURE:
<221> NAME/KEY: MOD_RES
<222> LOCATION: (2)..(3)
<223> OTHER INFORMATION: D-Lys
<220> FEATURE:
<223> OTHER INFORMATION: C-term PNA modified
<220> FEATURE:
<223> OTHER INFORMATION: See specification as filed for detailed
      description of substitutions and preferred embodiments

<400> SEQUENCE: 1

Lys Lys Lys
1

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      peptide nucleic acid sequence
<220> FEATURE:
<223> OTHER INFORMATION: 5' PNA modified
<220> FEATURE:
<221> NAME/KEY: misc_feature
<222> LOCATION: (1)..(18)
<223> OTHER INFORMATION: PNA sequence
<220> FEATURE:
<223> OTHER INFORMATION: 3' PNA modified

<400> SEQUENCE: 2
cctcaagagt aataatat                                                   18

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PNA modified
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Pro
<220> FEATURE:
<221> NAME/KEY: MOD_RES
<222> LOCATION: (3)..(5)
<223> OTHER INFORMATION: D-Lys
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Lys
<220> FEATURE:
<221> NAME/KEY: MOD_RES
<222> LOCATION: (8)..(8)
```

```
<223> OTHER INFORMATION: D-Val
<220> FEATURE:
<221> NAME/KEY: MOD_RES
<222> LOCATION: (9)..(10)
<223> OTHER INFORMATION: D-Lys
<220> FEATURE:
<221> NAME/KEY: MOD_RES
<222> LOCATION: (11)..(11)
<223> OTHER INFORMATION: Lys(palmitoyl)
<220> FEATURE:
<223> OTHER INFORMATION: C-term CONH2
<220> FEATURE:
<223> OTHER INFORMATION: See specification as filed for detailed
      description of substitutions and preferred embodiments

<400> SEQUENCE: 3

Lys Pro Lys Lys Lys Arg Lys Val Lys Lys Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PNA modified
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Arg3
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Arg2
<220> FEATURE:
<221> NAME/KEY: MOD_RES
<222> LOCATION: (5)..(5)
<223> OTHER INFORMATION: D-Lys2
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (8)..(8)
<223> OTHER INFORMATION: D-Tyr
<220> FEATURE:
<221> NAME/KEY: MOD_RES
<222> LOCATION: (9)..(10)
<223> OTHER INFORMATION: D-Lys
<220> FEATURE:
<221> NAME/KEY: MOD_RES
<222> LOCATION: (11)..(11)
<223> OTHER INFORMATION: Lys(palmitoyl)
<220> FEATURE:
<223> OTHER INFORMATION: C-term CONH2
<220> FEATURE:
<223> OTHER INFORMATION: See specification as filed for detailed
      description of substitutions and preferred embodiments

<400> SEQUENCE: 4

Lys Arg Gln Arg Lys Arg Gly Tyr Lys Lys Lys
1               5                   10
```

METHODS AND COMPOSITIONS FOR TREATING CANCER USING PEPTIDE NUCLEIC ACID-BASED AGENTS

CROSS REFERENCES TO RELATED APPLICATIONS

The present application claims priority to U.S. Provisional Patent Application No. 61/920,289, filed on Dec. 23, 2013. This provisional application is incorporated herein by reference in its entirety.

BACKGROUND

The healthcare industry experiences a constant need to provide new and effective therapies for treating patients battling cancer. The discovery of novel compositions that deviate from traditional chemotherapeutic approaches are aiding in the approach physicians use to prescribe course of treatments for oncology patients. Particular effort is directed toward compositions and methods for treating cancer using molecular biological approaches rather than chemical approaches.

SUMMARY

The present invention provides new and effective compositions for treating cancer. Among other things, the present invention recognizes the source of a problem with conventional cancer treatments and provides the insight that compounds which target gene (e.g., oncogene) expression, as described herein, are particularly useful in various contexts for treating cancer.

Among other things, the present disclosure demonstrates that peptide nucleic acid (PNA) agents that can specifically target genes, can enable improved treatments for cancer. In some embodiments, use of peptide nucleic acid agents will enable improved methods for suppressing and treating cancer within a clinical setting. Furthermore, peptide nucleic acids with terminal cationic and/or hydrophobic moieties that improve solubility within cell membranes can be more effective at crossing cellular membranes than previous PNA-type agents and offer stabilization toward the anionic chromosomal target.

PNA agents are promising tools in the research and development of new drugs to treat diseases such as cancer. The present disclosure provides improved PNA agents, as well as technologies for designing, identifying, characterizing and/or using them, and compositions that include them.

Among other things, the present invention encompasses the recognition that one unmet need in use of available PNA-based drugs is the successful delivery of agents across cellular membranes to the target gene. For example, the ability to cross cell membranes is mediated by cationic/hydrophobic delivery peptides. Among other things, the present invention discloses PNA agents whose physiochemical properties contribute to improved drug delivery across cell membranes (e.g., relative to available PNA agents).

For example, the present disclosure demonstrates that cationically charged termini on PNA agents improve the ability to target non-promoter regions of genes, which are less open and exposed compared to promoter regions. Without wishing to be bound by any particular theory, the present disclosure proposes that stabilizing the cationically charged lysine-derivatized PNA termini against the anionic DNA improves a PNA's binding kinetics to targets. These terminal modifications allow stabilization of the conjugate termini towards the chromosomal anionic phosphate esters due to cationic-anionic interaction as depicted in FIG. 1A. This aids a PNA's strand-invading properties and allows it to displace the complementary strand of its oncogene target. According to the Zimm-Bragg statistical helical model, stabilization of the configurationally more labile portions (termini) towards helix formation is the most entropically disfavored step. Following stabilization of the terminus/termini, helix formation is comparatively immediate. This is also consistent with the stochastic chain model.

PNA agents of the present disclosure are modified relative to traditional PNA agents through use of cationic/hydrophobic peptides; in some embodiments, such modified PNA agents show improved delivery across cell membranes relative to that observed with otherwise comparable PNA agents that do not include such cationic/hydrophobic peptides. Again without wishing to be bound by any particular theory, the present disclosure proposes that hydrophobic and cationic terminal peptides together facilitate passive transport of inventive PNA agents across membranes. For example, in certain particular embodiments, hydrophobic e-palmitoyl lysine termini are driven together by solvent exclusion, and the PNA-peptide conjugate is intramolecularly further stabilized by pi-interacting nucleoside bases. In some embodiments, a PNA-peptide chain is compacted (i.e., displays a decreased radius of gyration) through such interactions, allowing it to more easily permeate a membrane (e.g., a lipid bilayer). Furthermore, it is hypothesized that cationic-anionic interactions between PNA agents of the present invention and phospholipids cell membrane also facilitate the PNA agent's insertion into the membrane.

With respect to PNA agents, there is a thermodynamic equilibrium between stable binding within a cell membrane and dissociating from the membrane. Without wishing to be bound by any particular theory, it is envisioned that the modifications of PNA agents of the present invention ease the kinetic barrier for membrane insertion of PNA agents so that the aforesaid equilibrium is more quickly achieved. This, in turn, accelerates transmembrane transport as depicted in FIG. 1B.

Without wishing to be bound by any particular theory, it is contemplated that a PNA-agent of the present invention exists in an equilibrium between folded and open states as depicted for example in FIG. 1C. The folded state lends itself well for cell membrane insertion, and the open-coil state lends itself well for helical association with chromosomal targets for a better facilitated helix-coil transition.

The art has developed a variety of strategies for transporting oligonucleotides across cell membranes. The present invention provides improved systems, permitting enhanced transport of provided PNA derivatives across cell membranes and intracellular delivery, and furthermore facilitating binding of PNA agents to and targeting of less exposed regions of DNA.

Embodiments of the present invention encompass the surprising discovery that peptide nucleic acid agents with modified termini as described herein can better cross cellular membranes and bind to target genes. According to some embodiments of the present invention, modified peptide nucleic acid agents specific for BRAF mutations, can suppress transcription and ultimately translation of mutant BRAF protein as well reduce viability of cells expressing the mutant protein.

Embodiments of the present invention encompass the surprising discovery that peptide nucleic acid agents can bind to genes associated with a disease state.

In some embodiments, the invention provides PNA agents comprising: a PNA moiety; a first cationic or hydrophobic moiety at a first end of the PNA moiety; and a second cationic or hydrophobic moiety at a second end of the PNA moiety. In some embodiments, the first cationic moiety is or comprises a peptide. In some embodiments, the first cationic peptide comprises or consists of lysine residues. In some embodiments, at least one lysine residue comprises a palmitoyl side chain moiety. In some embodiments, the first cationic peptide comprises amines.

In some embodiments, the invention provides PNA agents comprising: a PNA moiety; a first cationic moiety and a first hydrophobic moiety at a first end of the PNA moiety; and a second cationic moiety and a second hydrophobic moiety at a second end of the PNA moiety. In some embodiments, the first cationic and/or hydrophobic moiety is or comprises a peptide. In some embodiments, the second cationic and/or hydrophobic moiety is or comprises a peptide. In some embodiments, the first and/or second cationic peptide comprises one or more lysine residues. In some embodiments, the first and/or second hydrophobic peptide comprises one or more lysine residues. In some embodiments, at least one lysine residue comprises a palmitoyl side chain moiety. In some embodiments, at least one lysine residue at either end of the PNA moiety comprises a palmitoyl side chain moiety. In some embodiments, the first and/or second cationic and/or hydrophobic peptide comprises amines.

In some embodiments, the palmitoyl lysine is not attached to the PNA moiety directly, but via one or more additional amino acids.

In some embodiments, the PNA agent has a sequence that does not form hairpin loops. In some embodiments, the PNA agent has a sequence that has a tendency to not form hairpin loops. In some embodiments, the PNA agent has a sequence that contains less than 60% purines. In some embodiments, the first and/or second cationic and/or hydrophobic moiety is a targeting moiety in that the terminal cationic moieties more effectively align themselves with the DNA anionic phosphoribose. This allows them a greater statistical likelihood of finding the nucleic acid with the sequence to which they are targeted. The terminal hydrophobic/cationic residues more effectively ease the PNA derivative through cell membranes. The termini likely associate intramolecularly by 'hydrophobic solvent exclusion,' thus increasing the statistically high likelihood of the termini being within proximity of each other. In some embodiments, the second cationic or hydrophobic moiety is or comprises a cationic and/or hydrophobic peptide.

In some embodiments, the targeting moiety is at the PNA agent's N-terminus. In some embodiments, the cationic peptide is at the PNA agent's C-terminus. In some embodiments, the first cationic or hydrophobic moiety is a targeting moiety in that the terminal cationic moieties more effectively align themselves with the DNA anionic phosphoribose to allow a greater statistical likelihood of finding the nucleic acid with the sequence to which they are targeted and is attached at the PNA agent's N-terminus; and the second cationic or hydrophobic moiety is or comprises a cationic peptide that is attached at the PNA agent's C-terminus.

In some embodiments, PNA agents comprise a sequence that targets a gene. In some embodiments, PNA agents comprise a sequence that targets a 13-20 nucleotide sequence of a gene with 75% or greater complementarity. In some embodiments, PNA agents comprise a nucleic acid whose length is at least 14, 15, 16, 17, or 18 nucleotides and/or the complementarity is at least about 80%, 85%, 90%, 95%, 96%, 97%, 98%, 99%, or 100%. In some embodiments, the PNA agent has a sequence that targets a non-promoter region of a gene. In some embodiments, the gene is an oncogene. In some embodiments, the oncogene includes a mutant sequence element and the PNA agent has a sequence that targets a site comprising or consisting of the mutant sequence element.

In some embodiments, the PNA component incorporates a sense (mRNA) sequence of a target gene.

In some embodiments, the PNA agent is targeted to a region of a BRAF oncogene comprising a mutation corresponding to a V600E mutation in a BRAF protein. In some embodiments, the PNA agent is targeted to a region of a Gnaq gene comprising a mutation corresponding to a Q209L mutation in a Gnaq protein.

In some embodiments, the PNA agent is targeted to a region comprising a translocation junction of an oncogene. In some embodiments, the PNA agent is targeted to a region of a MYB-NFIB translocation comprising a junction of MYB and NFIB genes or fragments thereof. In some embodiments, the PNA agent is targeted to a region of a FUS-CHOP translocation comprising a junction of FUS and CHOP genes or fragments thereof.

In some embodiments, the PNA agent has a sequence that targets a site in a gene, which PNA agent is characterized in that, when a system comprising a cell that expresses the gene is exposed to the PNA agent, expression of the gene is reduced by an amount within the range of 20% to 90% suppression of normal activity when the PNA agent is present as compared with otherwise comparable conditions when it is absent. In some embodiments, the PNA agent has a sequence that targets a site in a gene, which PNA agent is characterized in that, when a system comprising a cell that expresses the gene is exposed to the PNA agent, expression of the gene is reduced by an amount within the range of 20% to 90% when the PNA agent is present as compared with otherwise comparable conditions when it is absent. In some embodiments, protein product is reduced to less than 50% expression. In some embodiments, the cell is a human cell. In some embodiments, the system is or comprises an animal. In some embodiments, the system is or comprises a primate. In some embodiments, the system is or comprises a human. In some embodiments, the system is or comprises a mouse. In some embodiments, the system is or comprises a genetically modified mouse. In some embodiments, the system is or comprises a BRAF mouse. In some embodiments, the system is or comprises the cell in culture.

In some embodiments, the PNA moiety has a length within the range of 13-18 nucleotides. In some embodiments, PNA moieties have palmitoyl lysine attached to the termini. In some embodiments, PNA moieties have palmitoyl lysine attached to both N- and C-termini. In some embodiments, PNA moieties have a delivery peptide length within the range of 8-12 amino acids. In some embodiments, PNA-peptide conjugates are intramolecularly stabilized by pi-interacting nucleoside bases. In some embodiments, the radius of gyration of the PNA agent is decreased within the range of 25% to 50%. In some embodiments, PNA agents, when contacted with a cell membrane, crosses the membrane 10 times as much as reference PNA agents lacking one or both terminal hydrophobic/cationic moieties. In some embodiments, gene suppression is approximately a magnitude more effective by employing cationic/hydrophobic Lys (palmitoyl)-Lys-Lys residues on both termini in comparison to a standard delivery peptide-PNA motif.

In some embodiments, a method for treating or reducing the risk of a disease, disorder, or condition comprising:

administering to a subject susceptible to the disease, disorder, or condition a PNA agent is provided. In some embodiments, the subject is suffering from or susceptible to cancer. In some embodiments, the cancer is selected from melanoma, ocular melanoma and/or sarcoma.

In some embodiments, methods of reducing expression of a target gene in a cell comprising: contacting a cell in which the target is expressed with at least one PNA agent; determining a level or activity of the target in the cell when the PNA agent is present as compared with a target reference level or activity observed under otherwise comparable conditions when it is absent; and classifying the at least one PNA agent as a target inhibitor if the level or activity of the target is significantly reduced when the PNA agent is present as compared with the target reference level or activity are provided.

In some embodiments, a method for identifying and/or characterizing PNA agents for target inhibition comprising: contacting a system in which a target is expressed with at least one PNA agent; determining a level or activity of the target in the system when the PNA agent is present as compared with a target reference level or activity observed under otherwise comparable conditions when it is absent; and classifying the at least one PNA agent as a target inhibitor if the level or activity of the target is significantly reduced when the PNA agent is present as compared with the target reference level or activity is provided.

Any of the methods disclosed herein may include administering or using any of the PNA agents disclosed herein.

In some embodiments, the level or activity of the target comprises a target mRNA level. In some embodiments, the level or activity of the target comprises a target protein level. In some embodiments, the system comprises an in vitro system. In some embodiments, the system comprises an in vivo system. In some embodiments, the system is or comprises cells.

In some embodiments, the level or activity of the target corresponds to cell viability. In some embodiments, a significant reduction in the level or activity of the target corresponds to a greater than 90% decrease in tumor cell viability.

In some embodiments, the cells comprise cancer cells. In some embodiments, the system comprises cells in cell culture. In some embodiments, the cells in cell culture comprise BRAF wild type cells. In some embodiments, BRAF wild type cells comprise C918 cells. In some embodiments, the cells in cell culture comprise BRAF V600E melanoma cells. In some embodiments, BRAF V600E melanoma cells are selected from OCM1A uveal melanoma cells and/or SK-MEL 7 cutaneous melanoma cells.

In some embodiments, the system is or comprises tissue. In some embodiments, the system is or comprises an organism. In some embodiments, the level or activity of the target corresponds to survival of the organism. In some embodiments, a significant reduction in the level or activity of the target comprises a greater than 50% increase in survival of the organism.

In some embodiments, the organism comprises a mouse. In some embodiments, the mouse comprises a BRAF mouse. In some embodiments, the mouse comprises a BRAF V600E mouse.

In some embodiments, a significant reduction in the level or activity of the target comprises a greater than 30% reduction of target activity. In some embodiments, a significant reduction in the level or activity of the target comprises a greater than 10%, 15%, 20%, 25%, 30%, 35%, 40%, 45%, 50%, 55%, 60%, 65%, 70%, 75%, 80%, 85%, 90%, 95%, 96%, 97%, 98%, 99% reduction of target levels. In some embodiments, a significant reduction in the level or activity of the target comprises a greater than two-fold, three-fold, four-fold, five-fold, six-fold, seven-fold, eight-fold, nine-fold, ten-fold, fifteen-fold, twenty-fold, forty-fold, fifty-fold, sixty-fold, seventy-fold, eighty-fold, ninety-fold, one hundred-fold, two hundred-fold, three hundred-fold, four hundred-fold, five hundred-fold, six hundred-fold, seven hundred-fold, eight hundred-fold, nine hundred-fold, one thousand-fold, two thousand-fold, three thousand-fold, four thousand-fold, five thousand-fold, six thousand-fold, seven thousand-fold, eight thousand-fold, nine thousand-fold, ten thousand-fold or more. In some embodiments, the reference level is a historical reference. In some embodiments, the historical reference is recorded in a tangible and/or computer-readable medium.

In some embodiments, the target is a region comprising a point mutation in an oncogene. In some embodiments, the target is a region of a BRAF oncogene comprising a mutation corresponding to a V600E mutation in a BRAF protein. In some embodiments, the target is a region of a Gnaq gene comprising a mutation corresponding to a Q209L mutation in a Gnaq protein.

In some embodiments, the target is a region comprising a translocation junction of an oncogene. In some embodiments, the target is a MYB-NFIB translocation comprising a junction of MYB and NFIB genes or fragments thereof. In some embodiments, the target is a FUS-CHOP translocation comprising a junction of FUS and CHOP genes or fragments thereof.

In some embodiments, a pharmaceutical composition comprising the PNA agent and pharmaceutically acceptable carrier is provided. In some embodiments, the pharmaceutical composition is formulated for direct administration into a target tissue. In some embodiments, the pharmaceutical composition is formulated for oral administration. In some embodiments, the pharmaceutical composition is formulated for parenteral administration. In some embodiments, the pharmaceutical composition is formulated for intradermal administration. In some embodiments, the pharmaceutical composition is formulated for transdermal administration. In some embodiments, the pharmaceutical composition is formulated for administration by inhalation.

In some embodiments, the pharmaceutical composition is or comprises a liquid. In some embodiments, the pharmaceutical composition is or comprises a solid.

Additional features and advantages of the invention will be apparent from the following figures, definitions, detailed description and the claims.

DESCRIPTION OF THE DRAWING

The Figures described below, that together make up the Drawing, are for illustration purposes only, not for limitation.

FIG. 1—FIG. 1A shows schematic depictions of a PNA agent according to the present invention targeting DNA.

FIG. 2 shows data from a cell viability assay performed on melanoma cell lines that had been treated with increasing doses of indicated PNA agents for 72 hours. Cell viability was measured and calculated relative to the untreated cells.

FIG. 3 depicts BRAF mutant and BRAF wild type protein expression in melanoma cells treated with 750 nM of PNA agent PNA I-292-3 L2LP NHAc (which incorporates an NLS delivery peptide) over the periods of time indicated.

FIG. 4 depicts BRAF mutant and BRAF wild type protein expression in melanoma cells treated with 750 nM of PNA agent PNA I-292-9 L2 NHAc (which incorporates a TAT delivery peptide).

FIG. 5 depicts mRNA expression in cells wild type for BRAF (C918) and mutant cell lines (OCM1A and SK-Mel 7).

FIG. 6 shows data from xenograft mouse model studies employing OCM1A cells.

DEFINITIONS

Figure 1A:
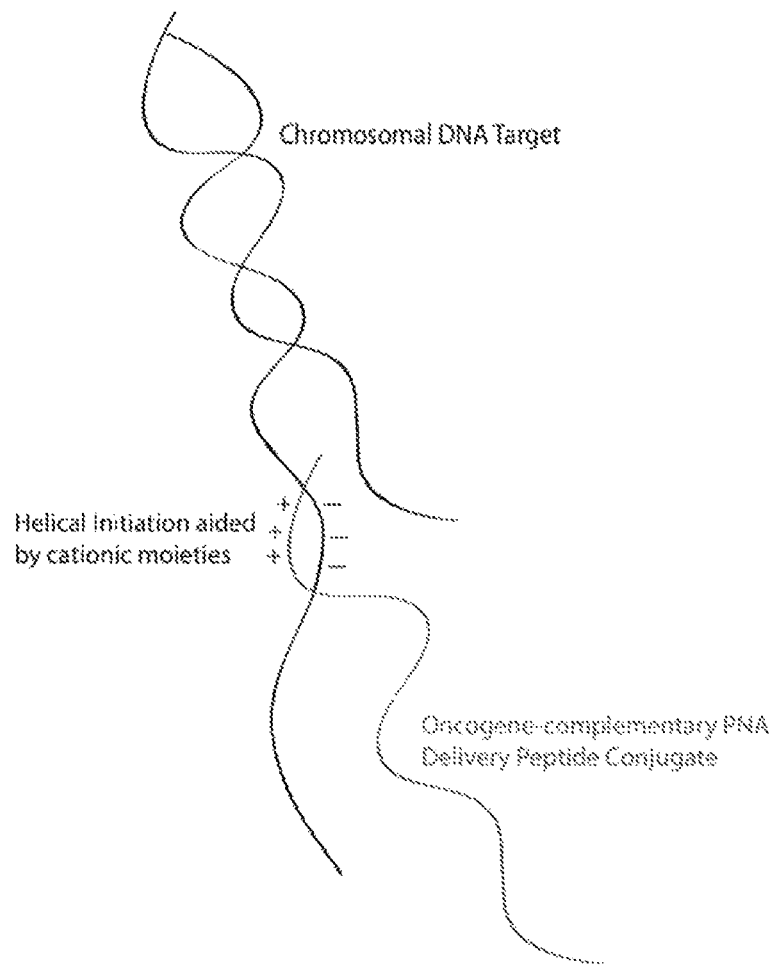
Figure 1B:
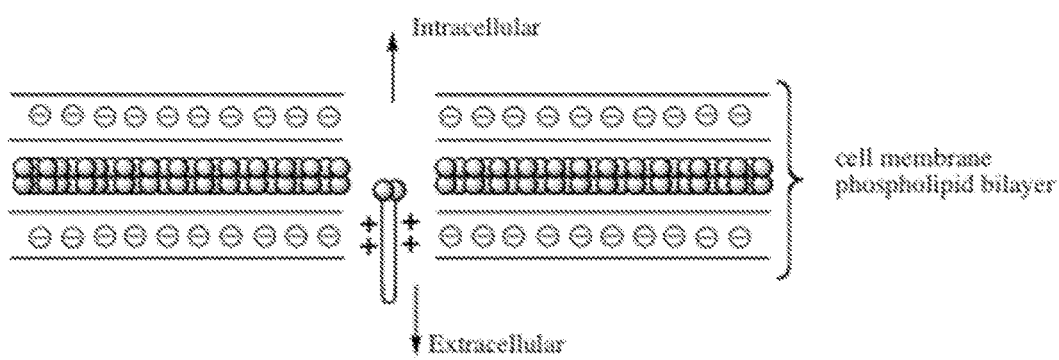
FIG. 1B shows a schematic depiction of a PNA agent according to the present invention crossing a cell membrane.
Figure 1C:
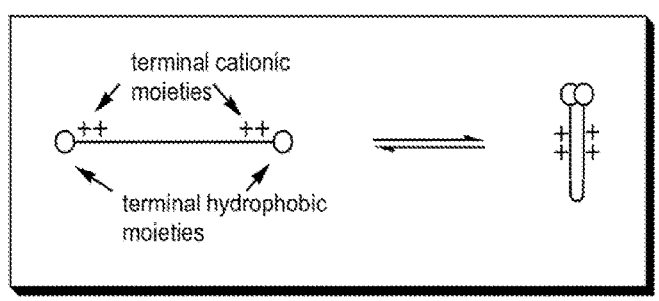
FIG. 1C shows a schematic depiction of different states of a PNA agent according to the present invention.

Agent: The term "agent" as used herein may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, siRNAs, shRNAs, DNA/RNA hybrids, antisense oligonucleotides, ribozymes, peptides, peptide mimetics, peptide nucleic acids, small molecules, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Affinity: As is known in the art, "affinity" is a measure of the tightness with a particular ligand (e.g., an HA polypeptide) binds to its partner (e.g., an HA receptor). Affinities can be measured in different ways. In some embodiments, affinity is measured by a quantitative assay (e.g., glycan binding assays). In some such embodiments, binding partner concentration (e.g., HA receptor, glycan, etc.) may be fixed to be in excess of ligand (e.g., an HA polypeptide) concentration so as to mimic physiological conditions (e.g., viral HA binding to cell surface glycans). Alternatively or additionally, in some embodiments, binding partner (e.g., HA receptor, glycan, etc.) concentration and/or ligand (e.g., an HA polypeptide) concentration may be varied. In some such embodiments, affinity (e.g., binding affinity) may be compared to a reference (e.g., a wild-type HA that mediates infection of a humans) under comparable conditions (e.g., concentrations).

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide. Animal: As used herein, the term "animal" refers to any member of the animal kingdom. In some embodiments, "animal" refers to humans, of either sex and at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, the animal is susceptible to infection by HCV. In some embodiments, an animal may be a transgenic animal, genetically engineered animal, and/or a clone.

Antibody agent: As used herein, the term "antibody agent" refers to an agent that specifically binds to a particular antigen. In some embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In some embodiments, the term encompasses monobodies or adnectins. In some embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Antagonist: As used herein, the term "antagonist" refers to an agent that i) inhibits, decreases or reduces the effects of another agent, for example that inactivates a nucleic acid; and/or ii) inhibits, decreases, reduces, or delays one or more biological events, for example, expression of one or more nucleic acids or stimulation of one or more biological pathways. Antagonists may be or include agents of any chemical class including, for example, small molecules, polypeptides, nucleic acids, carbohydrates, lipids, metals, and/or any other entity that shows the relevant inhibitory activity. An antagonist may be direct (in which case it exerts its influence directly upon the receptor) or indirect (in which case it exerts its influence by other than binding to the receptor; e.g., altering expression or translation of the receptor; altering signal transduction pathways that are directly activated by the receptor, altering expression, translation or activity of an agonist of the receptor).

Antibody polypeptide: As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain which is homologous or largely homologous to an immunoglobulin-binding domain. In some embodiments, "antibody polypeptides" encompasses polypeptides having a binding domain that shows at least 99% identity with an immunoglobulin binding domain. In some embodiments, "antibody polypeptide" is any protein having a binding domain that shows at least 70%, 80%, 85%, 90%, or 95% identity with an immunoglobulin binding domain, for example a reference immunoglobulin binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In some embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In some embodiments, the "antibody polypeptide" is an antibody fragment that retains at least a significant portion of the full-length antibody's specific binding ability. Examples of antibody fragments include, but are not limited to, Fab, Fab', F(ab')2, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, the antibody polypeptides may be a humanized. Humanized antibody polypeptides include may be chimeric immunoglobulins, immunoglobulin chains or antibody polypeptides (such as Fv, Fab, Fab', F(ab')2 or other antigen-binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity.

Antigen: An "antigen" is a molecule or entity to which an antibody binds. In some embodiments, an antigen is or comprises a polypeptide or portion thereof. In some embodiments, an antigen is a portion of an infectious agent that is recognized by antibodies. In some embodiments, an antigen is an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer other than a biologic polymer (e.g., other than a nucleic acid or amino acid polymer) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is or comprises a recombinant antigen.

Approximately: As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. In some embodiments, where a protein or polypeptide is biologically active, a portion of that protein or polypeptide that shares at least one biological activity of the protein or polypeptide is typically referred to as a "biologically active" portion.

Characteristic portion: As used herein, the term a "characteristic portion" of a substance, in the broadest sense, is one that shares some degree of sequence or structural identity with respect to the whole substance. In some embodiments, a characteristic portion shares at least one functional characteristic with the intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance; epitope-binding specificity is one example. In some embodiments, a characteristic portion may be biologically active.

Combination therapy: The term "combination therapy", as used herein, refers to those situations in which two or more different pharmaceutical agents for the treatment of disease are administered in overlapping regimens so that the subject is simultaneously exposed to at least two agents. In some embodiments, the different agents are administered simultaneously. In some embodiments, the administration of one agent overlaps the administration of at least one other agent. In some embodiments, the different agents are administered sequentially such that the agents have simultaneous biologically activity with in a subject.

Detection entity: The term "detection entity" as used herein refers to any element, molecule, functional group, compound, fragments thereof or moiety that facilitates detection of an agent (e.g., an antibody) to which it is joined. Examples of detection entities include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

Diagnostic information: As used herein, diagnostic information or information for use in diagnosis is any information that is useful in determining whether a patient has a disease or condition and/or in classifying the disease or condition into a phenotypic category or any category having significance with regard to prognosis of the disease or condition, or likely response to treatment (either treatment in general or any particular treatment) of the disease or condition. Similarly, diagnosis refers to providing any type of diagnostic information, including, but not limited to, whether a subject is likely to have a disease or condition (such as cancer), state, staging or characteristic of the disease or condition as manifested in the subject, information related to the nature or classification of a tumor, information related to prognosis and/or information useful in selecting an appropriate treatment. Selection of treatment may include the choice of a particular therapeutic (e.g., chemotherapeutic) agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

Dosage form: As used herein, the terms "dosage form" and "unit dosage form" refer to a physically discrete unit of a therapeutic composition to be administered to a subject. Each unit contains a predetermined quantity of active material (e.g., a therapeutic agent). In some embodiments, the predetermined quantity is one that has been correlated with a desired therapeutic effect when administered as a dose in a dosing regimen. Those of ordinary skill in the art appreciate that the total amount of a therapeutic composition or agent administered to a particular subject is determined by one or more attending physicians and may involve administration of multiple dosage forms.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a dosing regimen is or has been correlated with a desired therapeutic outcome, when administered across a population of patients.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Gene: As used herein, the term "gene" has its meaning as understood in the art. In some embodiments, the term "gene" may include gene regulatory sequences (e.g., promoters, enhancers, etc.) and/or intron sequences. In some embodiments, the term refers to nucleic acids that do not encode proteins but rather encode functional RNA molecules such as tRNAs, RNAi-inducing agents, etc. Alternatively or additionally, in some embodiments, the term "gene", as used in the present application, refers to a portion of a nucleic acid that encodes a protein. Whether the term encompasses other sequences (e.g., non-coding sequences, regulatory sequences, etc) will be clear from context to those of ordinary skill in the art.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the term "homology" refers to the overall relatedness between polymeric molecules, e.g., between polypeptide molecules. In some embodiments, polymeric molecules such as antibodies are considered to be "homologous" to one another if their sequences are at least 80%, 85%, 90%, 95%, or 99% identical. In some embodiments, polymeric molecules are considered to be "homologous" to one another if their sequences are at least 80%, 85%, 90%, 95%, or 99% similar.

Lysine or lysine residue: As used herein, the term "lysine" or "lysine residue" refers to the basic amino acid residue and its derivatives. Such derivatives include those lysine residues with side chain modifications. Lysine derivatives include e-palmitoyl lysine or Lys(palmitoyl-(dLys)2.

Marker: A marker, as used herein, refers to an agent whose presence or level is a characteristic of a particular tumor or metastatic disease thereof. For example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Mutant: As used herein, the term "mutant" refers to any alteration in a nucleic acid (or optionally genetic) sequence compared to its naturally-occurring counterpart. Mutant may also refer to the gene product (such as a protein), cells, or organism that possesses the mutated gene. Nucleic acid sequences possessing mutations can also be referred to as mutant sequence elements.

Non-promoter region: As used herein, the term "non-promoter region" refers to those section(s) of genes that are not sites of initiation of transcription. Unlike promoter regions, non-promoter regions tend to be closed off and less accessible to other elements.

Oncogene: As used herein, the term "oncogene" refers to those genes whose products are associated with causing cancer, dysplasia, hyperplasia, etc. in an organism. Oncogenes of the present disclosure may include, but are not limited to: ABL1, ABL2, ALK, AKT1, AKT2, ATF1, BCL11A, BCL2, BLC3, BCL6, BCR, BRAF, CARD11, CBLB, CBLC, CCND1, CCND2, CCND3, CDX2, CTNNB1, DDB2, DDIT3, DDX6, DEK, EGFR, ELK4, ERBB2, ETV4, ETV6, EVI1, EWSR1, FEV, FGFR1, FGFR1OP, FGFR2, FUS, GOLGA5, HMGA1, HMGA2, HRAS, IRF4, IDH1, IDH2, JUN, KIT, KRAS, LCK, LMO2, MAF, MAFB, MAML2, MDM2, MET, MITF, MLL, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, TLX1, TPR, and USP6.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, such cancer or tumor is or comprises a cancer of the prostate, or tumor in the prostate. In some embodiments, the disorder or condition is metastatic cancer. In some embodiments, the disorder or condition is melanoma.

Peptide: The term "peptide" refers to two or more amino acids joined to each other by peptide bonds or modified peptide bonds. In some embodiments, "peptide" refers to a polypeptide having a length of less than about 100 amino acids, less than about 50 amino acids, less than 20 amino acids, or less than 10 amino acids.

Peptide nucleic acid: The term "peptide nucleic acid" refers to synthetic polymers similar to DNA or RNA, but lacking deoxyribose and ribose sugar backbones, respectively. Peptide nucleic acids possess a backbone composed of repeating N-(2-aminoethyl)-glycine units linked by peptide bonds. Purine and pyrimidine bases are linked to the backbone by a methylene bridge and carbonyl group.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Prognostic and predictive information: As used herein, the terms prognostic and predictive information are used interchangeably to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Promoter: As used herein, the term "promoter" refers to regions of DNA that serve as initiation sites for transcription of a particular gene. Promoter sequences are often open/unraveled and await binding to other elements.

Protein: As used herein, the term "protein" refers to a polypeptide (i.e., a string of at least 3-5 amino acids linked to one another by peptide bonds). Proteins may include moieties other than amino acids (e.g., may be glycoproteins, proteoglycans, etc.) and/or may be otherwise processed or modified. In some embodiments "protein" can be a complete polypeptide as produced by and/or active in a cell (with or without a signal sequence); in some embodiments, a "protein" is or comprises a characteristic portion such as a polypeptide as produced by and/or active in a cell. In some embodiments, a protein includes more than one polypeptide chain. For example, polypeptide chains may be linked by one or more disulfide bonds or associated by other means. In some embodiments, proteins or polypeptides as described herein may contain L-amino acids, D-amino acids, or both, and/or may contain any of a variety of amino acid modifications or analogs known in the art. Useful modifications include, e.g., terminal acetylation, amidation, methylation, etc. In some embodiments, proteins or polypeptides may comprise natural amino acids, non-natural amino acids, synthetic amino acids, and/or combinations thereof. In some embodiments, proteins are or comprise antibodies, antibody polypeptides, antibody fragments, biologically active portions thereof, and/or characteristic portions thereof.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.,* 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Sample: As used herein, a sample obtained from a subject may include, but is not limited to, any or all of the following: a cell or cells, a portion of tissue, blood, serum, ascites, urine, saliva, and other body fluids, secretions, or excretions. The term "sample" also includes any material derived by processing such a sample. Derived samples may include nucleotide molecules or polypeptides extracted from the sample or obtained by subjecting the sample to techniques such as amplification or reverse transcription of mRNA, etc.

Specific binding: As used herein, the terms "specific binding" or "specific for" or "specific to" refer to an interaction (typically non-covalent) between a target entity (e.g., a target protein or polypeptide) and a binding agent (e.g., an antibody, such as a provided antibody). As will be understood by those of ordinary skill, an interaction is considered to be "specific" if it is favored in the presence of alternative interactions. In some embodiments, an interaction is typically dependent upon the presence of a particular structural feature of the target molecule such as an antigenic determinant or epitope recognized by the binding molecule. For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies having a sufficient degree of specificity to perform appropriately in any given application (e.g., for detection of a target molecule, for therapeutic purposes, etc.). Specificity may be evaluated in the context of additional factors such as the affinity of the binding molecule for the target molecule versus the affinity of the binding molecule for other targets (e.g., competitors). If a binding molecule exhibits a high affinity for a target molecule that it is desired to detect and low affinity for non-target molecules, the antibody will likely be an acceptable reagent for immunodiagnostic purposes. Once the specificity of a binding molecule is established in one or more contexts, it may be employed in other, preferably similar, contexts without necessarily re-evaluating its specificity.

Stage of cancer: As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition (cancer) has been diagnosed with and/or exhibits one or more symptoms of the disease, disorder, or condition. In some embodiments, an individual who is suffering from cancer is an individual who has increased tumor-associated or intratumoral cancer-related markers relative to an individual who does not have cancer.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. Many cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" refers to any agent that has a therapeutic effect and/or elicits a desired biological and/or pharmacological effect, when administered to a subject.

Therapeutically effective amount: As used herein, the term "therapeutically effective amount" refers to an amount of a therapeutic protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose)

for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The terms PNA and PNA moiety are used interchangeably herein. The terms PNA agent and PNA derivative are used interchangeably herein.

DETAILED DESCRIPTION OF CERTAIN EMBODIMENTS

The present invention is based, in part, upon the discovery that it is possible to produce peptide nucleic acid (PNA) agents that efficiently cross cell membranes and specifically target and suppress genes. Modifications to PNA agents improve the transmembrane permeability, target binding stability, solubility and specificity for target genes with specific sequences.

In some embodiments, PNA agents comprising: a PNA-moiety; and a first cationic and/or hydrophobic moiety at a first end of the PNA moiety; and a second cationic and/or hydrophobic moiety at a second end of the PNA moiety are provided. In some embodiments, PNA agents wherein the first and/or second cationic and/or hydrophobic moiety is or comprises a peptide are provided. In some embodiments, the first and/or second cationic and/or hydrophobic peptide comprises or consists of lysine residues. In some embodiments, at least one lysine residue comprises a palmitoyl side chain moiety. In some embodiments, the first and/or second cationic and/or hydrophobic peptide comprises amines. In some embodiments, PNA agents have a sequence that does not form hairpin loops. In some embodiments, PNA agents should have a sequence that does not form hairpin loops. In some embodiments, PNA agents should have a sequence that contains less than 60% purines.

In some embodiments, the first and/or second cationic and/or hydrophobic moiety is a targeting and delivery moiety that aids delivery of PNA through the cell membrane whereas the cationic moiety guides stability of the PNA against the target phosphate backbone. In some embodiments, the second cationic and/or hydrophobic moiety is or comprises a second cationic peptide which functions in the same capacity as the first cationic/hydrophobic moiety. In some embodiments, the cationic and/or hydrophobic moiety is at the PNA agent's N-terminus. In some embodiments, the targeting, or hydrophobic and/or cationic moiety is at the PNA agent's C-terminus. In some embodiments, the first cationic and/or hydrophobic moiety is a targeting moiety that aids delivery of PNA through the cell membrane and is attached at the PNA agent's N-terminus; and the second cationic and/or hydrophobic moiety is or comprises a cationic peptide that is attached at the PNA agent's C-terminus and guides stability of the PNA against the target phosphate backbone. In some embodiments, a second cationic peptide N-terminal to the PNA peptide and C-terminal to the targeting moiety is provided.

In some embodiments, PNA agents having a sequence that targets a gene are provided. In some embodiments, PNA agents have a sequence that targets a 13-20 nucleotide sequence of a gene with 75% or greater complementarity. In some embodiments, PNA agents have a sequence that targets a nucleic acid whose length is at least 14, 15, 16, 17, or 18 nucleotides and/or the complementarity is at least about 80%, 85%, 90%, 95%, 96%, 97%, 98%, 99%, or 100%.

In some embodiments, the PNA component incorporates a sense (mRNA) sequence of a target gene.

In some embodiments, PNA agents have a sequence that targets a non-promoter region of a gene. In some embodiments, the gene is an oncogene. In some embodiments, oncogenes include a mutant sequence element and PNA agents have a sequence that targets a site comprising or consisting of the mutant sequence element.

In some embodiments, PNA agents target a site comprising or consisting of a region of a BRAF oncogene comprising a mutation corresponding to a V600E mutation in a BRAF protein. In some embodiments, PNA agents targets a site comprising or consisting of a region of a Gnaq gene comprising a mutation corresponding to a Q209L mutation in a Gnaq protein.

In some embodiments, PNA agents target a site comprising or consisting of a region comprising a translocation junction of an oncogene. In some embodiments, PNA agents target a site comprising or consisting of a region of a MYB-NFIB translocation comprising a junction of MYB and NFIB genes or fragments thereof. In some embodiments, PNA agents target a site comprising or consisting of a region of a FUS-CHOP translocation comprising a junction of FUS and CHOP genes or fragments thereof. In some embodiments, PNA agents target a site comprising or consisting of a region of a EWS-FLI1 translocation comprising a junction of EWS and FLI1 genes or fragments thereof. In some embodiments, PNA agents target a site comprising or consisting of a region of a BCR-ABL translocation comprising a junction of BCR and ABL genes or fragments thereof. In some embodiments, PNA agents target a site comprising or consisting of a region of a SYT-SSX translocation comprising a junction of SYT and SSX genes or fragments thereof. In some embodiments, PNA agents target a translocation site comprising a juxtaposition/junction of two gene regions or a gene region which contains a point mutation or multiple point mutations.

In some embodiments, PNA agents target a site comprising or consisting of a region comprising an amplification of a gene. In some embodiments, PNA agents target gene amplifications comprising AKT2, CDK4, MDM2, MYCN, CCNE, CCND1, KRAS, HRAS, EGFR, ERBB2, ERBB1, FGF, FGFR1, FGFR2, MYC, MYB, and MET.

In some embodiments, PNA agents have a sequence that targets a site in a gene, which PNA agents are characterized in that, when a system comprising a cell that expresses the gene is exposed to the PNA agent, expression of the gene is reduced by an amount within the range of 50% to 100% when the PNA agent is present as compared with otherwise comparable conditions when it is absent. In some embodiments, the ideal range is dependent upon the response measured by decreased cell proliferation. In some embodiments, the cell is a human cell. In some embodiments, the system is or comprises an animal. In some embodiments, the system is or comprises a primate. In some embodiments, the system is or comprises a human. In some embodiments, the system is or comprises a BRAF mouse. In some embodiments, the system is or comprises the cell in culture.

In some embodiments, PNA moieties have a length within the range of 13-18 nucleotides. In some embodiments, PNA moieties have palmitoyl lysine attached to the termini. In some embodiments, PNA moieties have palmitoyl lysine attached to both N- and C-termini. In some embodiments, PNA moieties have a delivery peptide length within the range of 8-12 amino acids. In some embodiments, PNA-peptide conjugates are intramolecularly stabilized by pi-interacting nucleoside bases. In some embodiments, the radius of gyration of the PNA agent is decreased within the range of 25% to 50% by hydrophobic solvent exclusion driving the N- and C-terminal palmitoyl lysines proximal to each other. In some embodiments, PNA agents, when contacted with a cell membrane, crosses the membrane 10 times more quickly in comparison to reference PNA agents lacking one or both terminal hydrophobic/cationic moieties. In some embodiments, PNA agents cross membranes a magnitude more easily based upon results from cell proliferation experiments comparing with and without terminal palmitoyl lysines.

In some embodiments, a PNA moiety has a first cationic moiety and a first hydrophobic moiety at a first end, and a second cationic moiety and a second hydrophobic moiety at a second end, and the first cationic moiety and the first hydrophobic moiety at the first end are part of one amino acid, and the second cationic moiety and the second hydrophobic moiety at the second end are part of one amino acid.

In some embodiments, methods for treating or reducing the risk of a disease, disorder, or condition comprising: administering to a subject susceptible to the disease, disorder, or condition PNA agents are provided. In some embodiments, subjects suffering from or susceptible to cancer are provided. In some embodiments, cancers are selected from melanoma, ocular melanoma and/or sarcoma.

In some embodiments, methods of reducing expression of a target gene in a cell comprising: contacting a cell in which the target is expressed with at least one PNA agent; determining a level or activity of the target in the cell when the PNA agent is present as compared with a target reference level or activity observed under otherwise comparable conditions when it is absent; and classifying the at least one PNA agent as a target inhibitor if the level or activity of the target is significantly reduced when the PNA agent is present as compared with the target reference level or activity are provided.

In some embodiments, methods for identifying and/or characterizing PNA agents for target inhibition comprising: contacting a system in which a target is expressed with at least one PNA agent; determining a level or activity of the target in the system when the PNA agent is present as compared with a target reference level or activity observed under otherwise comparable conditions when it is absent; and classifying the at least one PNA agent as a target inhibitor if the level or activity of the target is significantly reduced when the PNA agent is present as compared with the target reference level or activity are provided. In some embodiments, suppressing a tumor-driving oncogene is measured by determining the activity level by the amount of suppression of cell proliferation; the suppression of oncogene mRNA; and the suppression of oncogene protein product. PNAs without any terminal (d)lysine-(d)lysine palmitoyl lysine, with one terminal (d)lysine-(d)lysine-palmitoyl lysine, and with both terminal (d)lysine-(d)lysine-palmitoyl lysine have been evaluated. In some embodiments, PNAs conjugated to NLS, TAT, or any other delivery peptide, incorporating both terminal (d)lysine-(d)lysine-palmitoyl lysine show significantly better gene suppression than those with only a single terminus derivatized or no termini derivatized.

In some embodiments, one or more of the following PNA agents may be used in connection with the present invention: PNAs with terminal peptides including tetra-substituted ammonium or tri-substituted sulfonium moieties.

In some embodiments, the level or activity of the target comprises a target mRNA level. In some embodiments, the level or activity of the target comprises a target protein level. In some embodiments, the level or activity of the target corresponds to cell viability. In some embodiments, a significant reduction in the level or activity of the target corresponds to a greater than 50% increase in cell viability. In some embodiments, complete suppression of gene expression is not necessary for significant suppression of cell proliferation/decreasing cell viability.

In some embodiments, the system comprises an in vitro system. In some embodiments, the system comprises an in vivo system. In some embodiments, the system is or comprises cells.

In some embodiments, the cells comprise cancer cells. In some embodiments, the system comprises cells in cell culture. In some embodiments, the cells in cell culture comprise BRAF wild type cells. In some embodiments, BRAF wild type cells comprise C918 cells. In some embodiments, the cells in cell culture comprise BRAF V600E melanoma cells. In some embodiments, BRAF V600E melanoma cells are selected from OCM1A uveal melanoma cells and/or SK-MEL 7 cutaneous melanoma cells.

In some embodiments, the system is or comprises tissue. In some embodiments, the system is or comprises an organism. In some embodiments, the level or activity of the target corresponds to survival of the organism. In some embodiments, a significant reduction in the level or activity of the target comprises a greater than 50% increase in survival of the organism. In some embodiments, the organism comprises a mouse. In some embodiments, the mouse comprises a BRAF mouse.

In some embodiments, a significant reduction in the level or activity of the target comprises a greater than 30-50% reduction of target activity. In some embodiments, a significant reduction in the level or activity of the target comprises a greater than 50-100% reduction of target activity. In some embodiments, a significant reduction in the level or activity of the target comprises a greater than 50% reduction of target levels. In some embodiments, reduction of gene target expression by 30-50% significantly reduces tumor cell proliferation in cell culture.

In some embodiments, the reference level is a historical reference. In some embodiments, the historical reference is recorded in a tangible and/or computer-readable medium.

In some embodiments, the target is a region comprising a point mutation in an oncogene. In some embodiments, the target is a region of a BRAF oncogene comprising a mutation corresponding to a V600E mutation in a BRAF protein.

In some embodiments, the target is a region of a Gnaq gene comprising a mutation corresponding to a Q209L mutation in a Gnaq protein. In some embodiments, the target is a region comprising a translocation junction of an oncogene. In some embodiments, the target is a MYB-NFIB translocation comprising a junction of MYB and NFIB genes or fragments thereof. In some embodiments, the target is a FUS-CHOP translocation comprising a junction of FUS and CHOP genes or fragments thereof. In some embodiments, the target is a BCR-ABL translocation comprising a junction of BCR and ABL genes or fragments thereof. In some embodiments, the target is a SYT-SSX translocation comprising a junction of SYT and SSX genes or fragments thereof. In some embodiments, the target is a region comprising a gene amplification. In some embodiments the gene amplification comprises an amplification of AKT2, CDK4, MDM2, MYCN, CCNE, CCND1, KRAS, HRAS, EGFR, ERBB2, ERBB1, FGF, FGFR1, FGFR2, MYC, MYB, and MET.

In some embodiments, a pharmaceutical composition comprising PNA agents and pharmaceutically acceptable carriers are provided. In some embodiments, pharmaceutical composition is formulated for direct administration into a target tissue. In some embodiments, the pharmaceutical composition is formulated for oral administration. In some embodiments, the pharmaceutical composition is formulated for parenteral administration. In some embodiments, the pharmaceutical composition is formulated for intradermal administration. In some embodiments, the pharmaceutical composition is formulated for transdermal administration. In some embodiments, the pharmaceutical composition is formulated for administration by inhalation. In some embodiments, the pharmaceutical composition is or comprises a liquid. In some embodiments, the pharmaceutical composition is or comprises a solid.

Peptide Nucleic Acid (PNA) Agent Structure

Peptide nucleic acids are synthetic polymers with similarities to DNA and RNA. PNAs possess backbones of repeating N-(2-aminoethyl)-glycine units that are linked by peptide bonds. PNAs are also called PNA moieties herein. This differs from backbones of DNA and RNA which are composed of deoxyribose and ribose sugar backbones, respectively. Furthermore, pyrimidine and purine bases are linked to the PNA backbone by carbonyl groups and methylene bridges. PNA backbones contain no charged phosphate groups. Therefore, due to a lack of electrostatic repulsion, binding between PNA sequences and DNA (or RNA) strands is stronger than binding between two DNA (or RNA) strands. Because of the higher binding strength, PNA oligomers longer than 20-25 bases are usually not necessary. Increasing the length of PNA strands could reduce specificity for target DNA (or RNA) sequences. A PNA/DNA mismatch has greater instability than a DNA/DNA mismatch; PNAs exhibit greater specificity than DNA when binding to complementary sequences. The lack of charged phosphate groups also contributes to the hydrophobic nature of PNAs, which cannot cross cellular membranes without some modification. These modifications can include, but are not limited to, covalently coupling a cell penetrating peptide and/or adding cationic/hydrophobic peptides. PNAs are also stable over a wide pH range and are resistant to enzyme degradation as they are not recognized by either proteases or nucleases.

In some embodiments, PNA agents are complementary to a target sequence. In some embodiments, they are exact copies of a mRNA sequence expressed by a gene of interest. In some embodiments, this is also the sense strand sequence of the gene. In some embodiments, PNA agents can be created complementary to any gene of interest.

Embodiments of the present invention are drawn to methods of improving the ability of PNA agents to cross cellular membranes. In some embodiments, the physico-chemical properties of the PNA agents have been modified to improve delivery across cell membranes by adding cationic/hydrophobic delivery peptides. In some embodiments, the hydrophobic and cationic terminal peptides together facilitate passive transport across membranes. PNA agents comprised of hydrophobic e-palmitoyl lysines at the termini have improved capabilities for crossing cellular membranes compared to standard PNA-peptide conjugates. In some embodiments, the terminal hydrophobic moieties in this design also allow the termini to be hydrophobically driven together decreasing the radius of gyration of the polymer. The smaller size allows for better transport. In some embodiments, having both ends of the PNA polymer derivatized more thoroughly imparts delivery functionalization of this large molecule. Hydrophobic e-palmitoyl lysine termini are driven together by solvent exclusion and the PNA-peptide conjugate is intramolecularly further stabilized by pi-interacting nucleoside bases. The PNA-peptide conjugate becomes more compact due to a decreased radius of gyration, thus allowing it to more easily permeate lipid bilayers. In some embodiments, the PNA agent is comprised of Lys(palmitoyl)-(dLys)2 at the N- and C-termini, bracketing a delivery peptide of ~10 amino acids in length and a ~15-18mer PNA. In some embodiments, the typical structure of PNA agents include: a delivery peptide of approximately 10 amino acids in length and a ~15-18mer PNA located within the bounds of two Lys(palmitoyl)-(dLys)2-termini attached by d-lysine. For example:

eg. Lys(palmitoyl)-(dLys)2-delivery peptide-PNA-(dLys)2-Lys(palmitoyl)

In some embodiments, PNA agents employ a modified NLS delivery peptide. In some embodiments, PNA agents employ a modified TAT delivery peptide.

In some embodiments, PNA agents used against a BRAF V600E target include:

```
AcNH-Lys(palmitoyl)-dLys-dLys-CCTCAAGAGTAATAATATdLys-dPro-dLys-dLys-dLys-dArg-dLys-dVal-dLys-dLys- Lys(palmitoyl)-CONH2 [I-292-3 L2LP (employing a NLS delivery peptide)]
and AcNH-Lys(palmitoyl)-dLys-dLys-CCTCAAGAGTAATAATATdLys-dArg3-dGln-dArg2-dLys2-dArg-Gly-dTyr-dLysdLys-Lys(palmitoyl)-CONH2. [I-292-9 L2 (employing a modified TAT delivery peptide)]
```

Gene Targeting

In some embodiments, the cationically charged termini improve the ability of the PNA to target genes with specific nucleic acid sequences. Stabilizing the cationically charged lysine-derivatized termini against the anionic DNA offers a kinetically faster binding by terminal nucleation as per the Zimm-Bragg statistical model. This enables the PNA to target non-promoter sequences in an improved manner, which is especially unexpected given that promoter sequences are usually open/unraveled and awaiting binding while non-promoter regions of genes are less accessible.

PNA is stabilized against its DNA target merely for lacking repulsive anionic phosphate-phosphate repulsive forces (enthalpic advantage). The cationic ends of the PNA-peptide improve the entropic component of binding by stabilizing the more configurationally free termini of the PNA-peptide against the target.

In some embodiments, the PNA of the PNA-peptide conjugate is of standard design—the length range is usually from 13-18 bases. For lengths less than 13 bases the binding becomes much less thermodynamically favorable due to decreased enthalpy of binding. For lengths greater than 18 bases do not offer more of a thermodynamic advantage as the gain in enthalpic binding energy is offset by the kinetic disadvantage of properly positioning such a long strand (more intramolecular substrates could compete with the binding state).

In some embodiments, the PNA agents target specific genes or genetic sequences. PNA agents can be designed to target genes possessing known mutated sequences as well as sites of genetic translocations. In some embodiments, the PNA agents target oncogenes. In some embodiments, the PNA agents can target mutant oncogenes. In some embodiments, wild type and mutant oncogenes that can be targeted are selected from the group comprising ABL1, ABL2, AKT1, AKT2, ALK, ATF1, BCL11A, BCL2, BLC3, BCL6, BCR, BRAF, CARD11, CBLB, CBLC, CCND1, CCND2, CCND3, CDX2, CTNNB1, DDB2, DDIT3, DDX6, DEK, EGFR, ELK4, ERBB2, ETV4, ETV6, EVI1, EWSR1, FEV, FGFR1, FGFR1OP, FGFR2, FUS, GOLGA5, HMGA1, HMGA2, HRAS, IDH1, IDH2, IRF4, JUN, KIT, KRAS, LCK, LMO2, MAF, MAFB, MAML2, MDM2, MET, MITF, MLL, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, TLX1, TPR, and USP6. In some embodiments, the oncogenes targeted comprise BRAF and Gnaq. In some embodiments, PNA agents can target sites of genetic abnormalities. In some embodiments, PNA agents can target sites of translocations. In some embodiments, sites of translocation can comprise the junction of the MYB-NFIB translocation. In some embodiments, sites of translocation can comprise the junction of the FUS-CHOP translocation. In some embodiments, sites of translocation can comprise the junction of the BCR-ABL translocation. In some embodiments, sites of translocation can comprise the junction of the SYT-SSX translocation. Any gene sequence can be targeted; PNA-peptide agents presented are destined for targeting against oncogenes comprised of single point mutations (and/or combinations thereof), gene translocation points, gene amplifications, or over expressed wild-type genes that drive tumors.

Systems for Testing PNA Agents

PNA agents can be tested in cancer lines as well as cell lines expressing genetic abnormalities. In some embodiments, PNA agents are tested in cancer cell lines. In some embodiments, PNA agents are tested in melanoma cell lines. In some embodiments, PNA agents are tested in uveal and cutaneous melanoma, and Ewings sarcoma cell lines. PNA agents can be tested in cell lines expressing a genetic abnormality associated with a disease other than cancer. PNA agents can be tested in neuronal and/or muscle cell lines with aberrant gene expression. In some embodiments, PNA agents are tested in rodent models comprising mutant gene sequences. In some embodiments, PNA agents may be tested in any cell line. A variety of cell lines are employed for testing PNA peptides by one of ordinary skill in the art.

Applications of PNA Agents

Targeting and binding by PNA agents would have uses as research tools, medical diagnostics and pharmaceutical treatments. In some embodiments, PNA agents can be used to target and bind specific genetic sequences. In some embodiments, PNA agents can be used to suppress expression of genetic sequences. PNA agents targeted to specific genes can serve as valuable research tools in understanding the function of those genes. Suppressing the expression of particular gene products would help elucidate and discover the role of those products in different biological pathways.

In some embodiments, PNA agents are used to target and suppress expression of BRAF genes. In some embodiments, PNA agents are used to target and suppress expression of mutant BRAF genes. In some embodiments, PNA agents are used to target and suppress expression of mutant Gnaq genes. In some embodiments, PNA agents can be used a treat diseases associated with genetic sequences. In some embodiments, PNA agents are used to treat diseases associated with mutated BRAF genes. In some embodiments, PNA agents are used to treat diseases associate with mutated Gnaq genes. In some embodiments, PNA agents are used to treat cancer.

In some embodiments, PNA agents are used to treat cancer in animals. In some embodiments, PNA agents are used to treat cancer in mammals. In some embodiments, PNA agents are used to treat cancer in primates. In some embodiments, PNA agents are used to treat cancer in humans.

PNA agents can target and bind to mutated genetic sequences and suppress the expression of mutant oncogenes, thereby suppressing and/or treating cancer. In some embodiments, PNA agents are used to treat cancer due to mutated BRAF genes. In some embodiments, PNA agents are used to treat cancer due to mutated Gnaq genes. In some embodiments, PNA agents are used to treat cancer due to translocations. PNA agents can target and bind to junctions of genetic translocations and suppress the expression of mutated genetic sequences, thereby preventing and/or treating translocation-associated cancer. Junctions of the MYB-NFIB translocation and the FUS-CHOP translocation can be targeted and suppressed by PNA agents of the present disclosure. Junctions of the BCR-ABL translocation and the SYT-SSX translocation can be targeted and suppressed by PNA agents of the present disclosure. PNA agents can target and bind to junctions of gene amplifications and suppress the expression of mutated genetic sequences, thereby preventing and/or treating amplification-associated cancer. Gene amplifications comprising the genes AKT2, CDK4, MDM2, MYCN, CCNE, CCND1, KRAS, HRAS, EGFR, ERBB2, ERBB1, FGF, FGFR1, FGFR2, MYC, MYB, and MET can be targeted and suppressed by PNA agents of the present disclosure.

PNA agents can be used to treat genetic abnormalities in diseases not associated with cancer. Diseases or conditions caused by a mutated gene product can treated by targeting a PNA agent to the mutated gene expressing the harmful gene product. Inherited or inborn disorders can be treated through the use of targeted PNA agents. PNA agents can be used to suppress normal genes such as those supportive of obesity, metabolic syndromes, or related vasculopathies. PNA agents can be used to target fungal genes, viral genes or bacterial genes causing infection.

Pharmaceutical Compositions

The present invention also provides compositions comprising one or more provided antibodies, fragments or characteristic portions thereof. In some embodiments, the present invention provides at least one PNA-conjugate and at least one pharmaceutically acceptable excipient. Such pharmaceutical compositions may optionally comprise and/or be administered in combination with one or more additional therapeutically or biologically active substances. In some embodiments, provided pharmaceutical compositions are useful in medicine or the manufacture of medicaments. In some embodiments, provided pharmaceutical compositions are useful as prophylactic agents (i.e., vaccines) in the treatment or prevention of cancer and neurodegenerative disorders thereof. In some embodiments, provided pharmaceutical compositions are useful in therapeutic applications, for example in individuals suffering from cancer; e.g., as delivery vehicles capable of specifically targeting cytotoxic agents or compounds that block aberrant cellular signaling. In some embodiments, the pharmaceutical compositions are simultaneously useful in diagnostic applications and therapeutic applications. In some embodiments, pharmaceutical compositions are formulated for administration to humans. In some embodiments, the pharmaceutical compositions comprise an antibody in combination with or conjugated to a therapeutic agent or other therapeutic as defined herein.

For example, pharmaceutical compositions may be provided in a sterile injectable form (e.g., a form that is suitable for subcutaneous injection or intravenous infusion). In some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservatives.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody compositions for longer than the specified time results in antibody degradation.

Liquid dosage forms and/or reconstituted solutions may comprise particulate matter and/or discoloration prior to administration. In some embodiments, a solution should not be used if discolored or cloudy and/or if particulate matter remains after filtration.

Pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient; for example, a peptide nucleic acid agent. The amount of the active ingredient is generally equal to a dose that would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

Conjugates Generally

Multifunctional agents described herein comprise multiple entities, each having at least one function. Certain embodiments of contemplated multifunctional agents comprise a targeting entity and at least one of the following entities: a detection entity, a therapeutic entity, and a diagnostic entity. In some embodiments, a multifunctional agent of the invention contains a targeting entity, a therapeutic entity and a detection entity. In some embodiments, the entities of an agent may be conjugated to one another. Conjugation of various entities to form a multifunctional agent is not limited to particular modes of conjugation. For example, two entities may be covalently conjugated directly to each other. Alternatively, two entities may be indirectly conjugated to each other, such as via a linker entity. In some embodiments, a multifunctional agent may include different types of conjugation within the agent, such that some entities of the agent are conjugated via direct conjugation while other entities of the agent are indirectly conjugated via one or more linkers. In some embodiments, a multifunctional agent of the invention comprises a single type of a linker entity. In some embodiments, a multifunctional agent of the invention comprises more than one type of linker entities. In some embodiments, a multifunctional agent includes a single type of linker entities but of varying length.

In some embodiments, there is a covalent association between or among entities contained in a multifunctional agent. As will be appreciated by one skilled in the art, the moieties may be attached to each other either directly or indirectly (e.g., through a linker, as described below).

In some embodiments, where one entity (such as a targeting entity) and a second entity of a multifunctional agent are directly covalently linked to each other, such direct covalent conjugation can be through a linkage (e.g., a linker or linking entity) such as an amide, ester, carbon-carbon, disulfide, carbamate, ether, thioether, urea, thiourea, isothiourea, amine, or carbonate linkage. Covalent conjugation can be achieved by taking advantage of functional groups present on the first entity and/or the second entity of the multifunctional agent. Alternatively, a non-critical amino acid may be replaced by another amino acid that will introduce a useful group (such as amino, carboxy or sulfhydryl) for coupling purposes. Alternatively, an additional amino acid may be added to at least one of the entities of the multifunctional agent to introduce a useful group (such as amino, carboxy or sulfhydryl) for coupling purposes. Suitable functional groups that can be used to attach moieties together include, but are not limited to, amines, anhydrides, hydroxyl groups, carboxy groups, thiols, and the like. An activating agent, such as a carbodiimide, can be used to form a direct linkage. A wide variety of activating agents are known in the art and are suitable for conjugating one entity to a second entity.

In some embodiments, entities of a multifunctional agent embraced by the present invention are indirectly covalently linked to each other via a linker group. Such a linker group may also be referred to as a linker or a linking entity. This can be accomplished by using any number of stable bifunctional agents well known in the art, including homofunctional and heterofunctional agents (for examples of such agents, see, e.g., Pierce Catalog and Handbook). The use of a bifunctional linker differs from the use of an activating agent in that the former results in a linking moiety being present in the resulting conjugate (agent), whereas the latter results in a direct coupling between the two moieties involved in the reaction. The role of a bifunctional linker may be to allow reaction between two otherwise inert moieties. Alternatively or additionally, the bifunctional linker that becomes part of the reaction product may be selected such that it confers some degree of conformational flexibility to the agent (e.g., the bifunctional linker comprises a straight alkyl chain containing several atoms, for example, the straight alkyl chain contains between 2 and 10 carbon atoms). Alternatively or additionally, the bifunctional linker may be selected such that the linkage formed between a provided antibody and therapeutic agent is cleavable, e.g., hydrolysable (for examples of such linkers, see e.g. U.S. Pat. Nos. 5,773,001; 5,739,116 and 5,877,296, each of which is incorporated herein by reference in its entirety). Such linkers, for example, may be used when higher activity of certain entities, such as a targeting agent and/or of a therapeutic entity is observed after hydrolysis of the conjugate. Exemplary mechanisms by which an entity may be cleaved from a multifunctional agent include hydrolysis in the acidic pH of the lysosomes (hydrazones, acetals, and cis-aconitate-like amides), peptide cleavage by lysosomal enzymes (the capthepsins and other lysosomal enzymes), and reduction of disulfides). Another mechanism by which such an entity is cleaved from the multifunctional agent includes hydrolysis at physiological pH extra- or intra-cellularly. This mechanism applies when the crosslinker used to couple one entity to another entity is a biodegradable/bioerodible component, such as polydextran and the like.

For example, hydrazone-containing multifunctional agents can be made with introduced carbonyl groups that provide the desired release properties. Multifunctional agents can also be made with a linker that comprises an alkyl chain with a disulfide group at one end and a hydrazine derivative at the other end. Linkers containing functional groups other than hydrazones also have the potential to be cleaved in the acidic milieu of lysosomes. For example, multifunctional agents can be made from thiol-reactive linkers that contain a group other than a hydrazone that is cleavable intracellularly, such as esters, amides, and acetals/ketals.

Another example of class of pH sensitive linkers are the cis-aconitates, which have a carboxylic acid group juxtaposed to an amide group. The carboxylic acid accelerates amide hydrolysis in the acidic lysosomes. Linkers that achieve a similar type of hydrolysis rate acceleration with several other types of structures can also be used.

Another potential release method for conjugates of the therapeutic agents is the enzymatic hydrolysis of peptides by the lysosomal enzymes. In one example, a provided antibody is attached via an amide bond to para-aminobenzyl alcohol and then a carbamate or carbonate is made between the benzyl alcohol and the therapeutic agent. Cleavage of the peptide leads to collapse of the amino benzyl carbamate or carbonate, and release of the therapeutic agent. In another example, a phenol can be cleaved by collapse of the linker instead of the carbamate. In another variation, disulfide reduction is used to initiate the collapse of a para-mercaptobenzyl carbamate or carbonate.

Useful linkers which may be used as a linking entity of a multifunctional agent provided herein include, without limitation: polyethylene glycol, a copolymer of ethylene glycol, a polypropylene glycol, a copolymer of propylene glycol, a carboxymethylcellulose, a polyvinyl pyrrolidone, a poly-1,3-dioxolane, a poly-1,3,6-trioxane, an ethylene/maleic anhydride copolymer, a polyaminoacid, a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group.

Some embodiments of the invention utilize multifunctional agents that include at least one non-covalently associated entity. Examples of non-covalent interactions include, but are not limited to, hydrophobic interactions, electrostatic interactions, dipole interactions, van der Waals interactions, and hydrogen bonding. Irrespective of the nature of the binding, interaction, or coupling, the association between a first entity and a second entity is, in some embodiments, selective, specific and strong enough so that the second entity contained in the agent does not dissociate from the first entity before or during transport/delivery to and into the target. Thus, association among multiple entities of a multifunctional agent may be achieved using any chemical, biochemical, enzymatic, or genetic coupling known to one skilled in the art.

Therapeutic Conjugates

As described herein, PNA agents may comprise part of multifunctional agents with therapeutic utility related to cancer or neurodegenerative disorders. Examples of therapeutic utilities in the context of the present disclosure include, without limitation, utility associated with targeting (e.g., binding specific gene sequences), utility associated with therapeutic effects (e.g., cytotoxic and/or cytostatic effects, anti-proliferative effects, anti-angiogenic effects, reducing symptoms etc.), and utility associated with diagnosis, detection or labeling, etc.

A targeting entity is a molecular structure that can be contained in an agent which affects or controls the site of action by specifically interacting with, or has affinity for, a target of interest. As an example, a target may be a molecule or molecular complex present on a cell surface, e.g., certain cell types, tissues, etc. In some embodiments of the invention, the target is tumor-associated or intratumoral gene and the targeting entity is a PNA agent. Use of targeting moieties for agents such as therapeutic agents is known in the art. In the context of the present application, primary or metastatic cancer cells, as well as other cell types, are the target. That is, at the molecular level, a target is a molecule or cellular constituent that is present (e.g., preferentially expressed) on a cell, such that it can specifically or preferentially bind to PNA agents upon contact. The PNA agents of the invention exert specificity for their target (e.g., oncogenes of cancer cells) and are able to localize to nuclei and bind to their target. In some embodiments, PNA agent targeting entities localize to cancer cells and retain their association over a period of time. In some embodiments, the PNA agent targets are the nucleic acid sequences encoding intratumoral and/or integral membrane proteins.

In some embodiments, the PNA agents are multifunctional agents comprising a gene targeting entity, which essentially consists of a PNA agent, conjugated to one or more therapeutic agents. Non-limiting embodiments of useful conjugates of PNA agents that may be used in the diagnosis or assessment of, treatment of and the manufacture of medicaments for cancer or other disorders are provided below.

Nucleic acid anti-cancer agents suitable for use in the practice of the present invention include those agents that target genes associated with tumorigenesis and cell growth or cell transformation (e.g., proto-oncogenes, which code for proteins that stimulate cell division), angiogenic/anti-angiogenic genes, tumor suppressor genes (which code for proteins that suppress cell division), genes encoding proteins associated with tumor growth and/or tumor migration, and suicide genes (which induce apoptosis or other forms of cell death), especially suicide genes that are most active in rapidly dividing cells.

Examples of genes associated with tumorigenesis and/or cell transformation include MLL fusion genes, BCR-ABL, TEL-AML1, EWS-FLI1, TLS-FUS, PAX3-FKHR, Bcl-2, AML1-ETO, AML1-MTG8, Ras, Fos PDGF, RET, APC, NF-1, Rb, p53, MDM2 and the like; overexpressed genes such as multidrug resistance genes; cyclins; beta-Catenin; telomerase genes; c-myc, n-myc, Bcl-2, Erb-B1 and Erb-B2; and mutated genes such as Ras, Mos, Raf, and Met. Examples of tumor suppressor genes include, but are not limited to, p53, p21, RB1, WT1, NF1, VHL, APC, DAP kinase, p16, ARF, Neurofibromin, and PTEN. Examples of genes that can be targeted by nucleic acid agents useful in anti-cancer therapy include genes encoding proteins associated with tumor migration such as integrins, selectins, and metalloproteinases; anti-angiogenic genes encoding proteins that promote formation of new vessels such as Vascular Endothelial Growth Factor (VEGF) or VEGFr; anti-angiogenic genes encoding proteins that inhibit neovascularization such as endostatin, angiostatin, and VEGF-R2; and genes encoding proteins such as interleukins, interferon, fibroblast growth factor ($\alpha$-FGF and ($\beta$-FGF), insulin-like growth factor (e.g., IGF-1 and IGF-2), Platelet-derived growth factor (PDGF), tumor necrosis factor (TNF), Transforming Growth Factor (e.g., TGF-$\alpha$ and TGF-$\beta$, Epidermal growth factor (EGF), Keratinocyte Growth Factor (KGF), stem cell factor and its receptor c-Kit (SCF/c-Kit) ligand, CD40L/CD40, VLA-4 VCAM-1, ICAM-1/LFA-1, hyalurin/CD44, and the like.

PNA agents may have any of a variety of uses including, for example, use as anti-cancer or other therapeutic agents, probes, primers, etc. Nucleic acid agents may have enzymatic activity (e.g., ribozyme activity), gene expression inhibitory activity (e.g., as antisense or siRNA agents, etc), and/or other activities. Nucleic acids agents may be active themselves or may be vectors that deliver active nucleic acid agents (e.g., through replication and/or transcription of a delivered nucleic acid). For purposes of the present specification, such vector nucleic acids are considered "therapeutic agents" if they encode or otherwise deliver a therapeutically active agent, even if they do not themselves have therapeutic activity.

In some embodiments, conjugates of PNA agents comprise a nucleic acid therapeutic agent that is a ribozyme. As used herein, the term "ribozyme" refers to a catalytic RNA molecule that can cleave other RNA or DNA molecules in a target-specific manner. Ribozymes can be used to downregulate the expression of any undesirable products of genes of interest. Examples of ribozymes that can be used in the practice of the present invention include, but are not limited to, those specific for oncogene mRNA or DNA.

In some embodiments, entities or moieties within conjugates of the PNA agents comprise a photosensitizer used in photodynamic therapy (PDT). In PDT, local or systemic administration of a photosensitizer to a patient is followed by irradiation with light that is absorbed by the photosensitizer in the tissue or organ to be treated. Light absorption by the photosensitizer generates reactive species (e.g., radicals) that are detrimental to cells. For maximal efficacy, a photosensitizer typically is in a form suitable for administration, and also in a form that can readily undergo cellular internalization at the target site, often with some degree of selectivity over normal tissues.

Conjugates of PNA agents associated with a photosensitizer can be used as new delivery systems in PDT. In addition to reducing photosensitizer aggregation, delivery of photosensitizers according to the present invention exhibits other advantages such as increased specificity for target tissues/organ and cellular internalization of the photosensitizer.

Photosensitizers suitable for use in the present invention include any of a variety of synthetic and naturally occurring molecules that have photosensitizing properties useful in PDT. In some embodiments, the absorption spectrum of the photosensitizer is in the visible range, typically between 350 nm and 1200 nm, preferably between 400 nm and 900 nm, e.g., between 600 nm and 900 nm. Suitable photosensitizers that can be coupled to toxins according to the present invention include, but are not limited to, porphyrins and porphyrin derivatives (e.g., chlorins, bacteriochlorins, isobacteriochlorins, phthalocyanines, and naphthalocyanines); metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid (R. W. Redmond and J. N. Gamlin, *Photochem. Photobiol.*, 1999, 70: 391-475).

Exemplary photosensitizers suitable for use in the present invention include those described in U.S. Pat. Nos. 5,171,741; 5,171,749; 5,173,504; 5,308,608; 5,405,957; 5,512,675; 5,726,304; 5,831,088; 5,929,105; and 5,880,145 (the contents of each of which are incorporated herein by reference in their entirety).

In some embodiments, conjugates of PNA agents comprise a radiosensitizer. As used herein, the term "radiosensitizer" refers to a molecule, compound or agent that makes tumor cells more sensitive to radiation therapy. Administration of a radiosensitizer to a patient receiving radiation therapy generally results in enhancement of the effects of radiation therapy. The advantage of coupling a radiosensitizer to a targeting entity (e.g., PNA agents capable of targeting intratumoral genetic sequences) is that the radiosensitize effects only on target cells. For ease of use, a radiosensitizer should also be able to find target cells even if it is administered systemically. However, currently available radiosensitizers are typically not selective for tumors, and they are distributed by diffusion in a mammalian body. PNA agents conjugates of the present invention can be used as a new delivery system for radiosensitizers.

A variety of radiosensitizers are known in the art. Examples of radiosensitizers suitable for use in the present invention include, but are not limited to, paclitaxel (TAXOL®), carboplatin, cisplatin, and oxaliplatin (Amorino et al., *Radiat. Oncol. Investig.*, 1999, 7: 343-352; Choy, *Oncology*, 1999, 13: 22-38; Safran et al., *Cancer Invest.*, 2001, 19: 1-7; Dionet et al., *Anticancer Res.*, 2002, 22: 721-725; Cividalli et al., *Radiat. Oncol. Biol. Phys.*, 2002, 52: 1092-1098); gemcitabine (Gemzar®) (Choy, *Oncology*, 2000, 14: 7-14; Mornex and Girard, *Annals of Oncology*, 2006, 17: 1743-1747); etanidazole (Nitrolmidazole®) (Inanami et al., *Int. J. Radiat. Biol.*, 2002, 78: 267-274); misonidazole (Tamulevicius et al., *Br. J. Radiology*, 1981, 54: 318-324; Palcic et al., *Radiat. Res.*, 1984, 100: 340-347), tirapazamine (Masunaga et al., *Br. J. Radiol.*, 2006, 79: 991-998; Rischin et al., *J. Clin. Oncol.*, 2001, 19: 535-542; Shulman et al., *Int. J. Radiat. Oncol. Biol. Phys.*, 1999, 44: 349-353); and nucleic acid base derivatives, e.g., halogenated purines or pyrimidines, such as 5-fluorodeoxyuridine (Buchholz et al., *Int. J. Radiat. Oncol. Biol. Phys.*, 1995, 32: 1053-1058).

In some embodiments, conjugates of PNA agents comprise a radioisotope. Examples of suitable radioisotopes include any α-, β- or γ-emitter, which, when localized at a tumor site, results in cell destruction (S. E. Order, "Analysis, Results, and Future Prospective of the Therapeutic Use of Radiolabeled Antibody in Cancer Therapy", Monoclonal Antibodies for Cancer Detection and Therapy, R. W. Baldwin et al. (Eds.), Academic Press, 1985). Examples of such radioisotopes include, but are not limited to, iodine-131 ($^{131}$I), iodine-125 ($^{125}$I), bismuth-212 ($^{212}$Bi), bismuth-213 ($^{213}$Bi), astatine-211 ($^{211}$At), rhenium-186 ($^{186}$Re), rhenium-188 ($^{188}$Re), phosphorus-32 ($^{32}$P), yttrium-90 ($^{90}$Y), samarium-153 ($^{153}$Sm), and lutetium-177 ($^{177}$Lu).

In some embodiments, conjugates of the PNA agents may be used in directed enzyme prodrug therapy. In a directed enzyme prodrug therapy approach, a directed/targeted enzyme and a prodrug are administered to a subject, wherein the targeted enzyme is specifically localized to a portion of the subject's body where it converts the prodrug into an active drug. The prodrug can be converted to an active drug in one step (by the targeted enzyme) or in more than one step. For example, the prodrug can be converted to a precursor of an active drug by the targeted enzyme. The precursor can then be converted into the active drug by, for example, the catalytic activity of one or more additional targeted enzymes, one or more non-targeted enzymes administered to the subject, one or more enzymes naturally present in the subject or at the target site in the subject (e.g., a protease, phosphatase, kinase or polymerase), by an agent that is administered to the subject, and/or by a chemical process that is not enzymatically catalyzed (e.g., oxidation, hydrolysis, isomerization, epimerization, etc.).

Some embodiments of the invention utilize PNA agent-directed enzyme prodrug therapy, wherein a PNA agent is linked to an enzyme and injected in a subject, resulting in selective binding of the enzyme to tumor-associated or metastatic genes. Subsequently, a prodrug is administered to the subject. The prodrug is converted to its active form by the enzyme only within or nearby the cancer cells. Selectivity is achieved by the specificity of the PNA agents and by delaying prodrug administration until there is a large differential between cancer and normal tissue enzyme levels. Cancer cells may also be targeted with the genes encoding for prodrug activating enzymes. This approach has been called virus-directed enzyme prodrug therapy (VDEPT) or more generally GDEPT (gene-directed enzyme prodrug therapy, and has shown good results in laboratory systems. Other versions of directed enzyme prodrug therapy include PDEPT (polymer-directed enzyme prodrug therapy), LEAPT (lectin-directed enzyme-activated prodrug therapy), and CDEPT (clostridial-directed enzyme prodrug therapy).

Nonlimiting examples of enzyme/prodrug/active drug combinations suitable for use in the present invention are described, for example, in Bagshawe et al., *Current Opinions in Immunology*, 1999, 11: 579-583; Wilman, "Prodrugs in Cancer Therapy", Biochemical Society Transactions, 14: 375-382, 615th Meeting, Belfast, 1986; Stella et al., "Prodrugs: A Chemical Approach To Targeted Drug Delivery", in "Directed Drug Delivery", Borchardt et al., (Eds), pp. 247-267 (Humana Press, 1985). Nonlimiting examples of enzyme/prodrug/active anti-cancer drug combinations are described, for example, in Rooseboom et al., *Pharmacol. Reviews*, 2004, 56: 53-102.

Examples of prodrug activating enzymes include, but are not limited to, nitroreductase, cytochrome P450, purine-nucleoside phosphorylase, thymidine kinase, alkaline phosphatase, β-glucuronidase, carboxypeptidase, penicillin amidase, β-lactamase, cytosine deaminase, and methionine γ-lyase.

Examples of anti-cancer drugs that can be formed in vivo by activation of a prodrug by a prodrug activating enzyme include, but are not limited to, 5-(aziridin-1-yl)-4-hydroxyl-amino-2-nitro-benzamide, isophosphoramide mustard, phosphoramide mustard, 2-fluoroadenine, 6-methylpurine, ganciclovir-triphosphate nucleotide, etoposide, mitomycin C, p-[N,N-bis(2-chloroethyl)amino]phenol (POM), doxorubicin, oxazolidinone, 9-aminocamptothecin, mustard, methotrexate, benzoic acid mustard, adriamycin, daunomycin, carminomycin, bleomycins, esperamicins, melphalan, palytoxin, 4-desacetylvinblastine-3-carboxylic acid hydrazide, phenylenediamine mustard, 4'-carboxyphthalato(1,2-cyclohexane-diamine) platinum, taxol, 5-fluorouracil, methylselenol, and carbonothionic difluoride.

In some embodiments, a therapeutic (e.g., anti-cancer) agent comprises a conjugate of one or more PNA agents and an anti-angiogenic agent. Antiangiogenic agents suitable for use in the present invention include any molecule, compound, or factor that blocks, inhibits, slows down, or reduces the process of angiogenesis, or the process by which new blood vessels form by developing from preexisting vessels. Such a molecule, compound, or factor can block angiogenesis by blocking, inhibiting, slowing down, or reducing any of the steps involved in angiogenesis, including (but not limited to) steps of (1) dissolution of the membrane of the originating vessel, (2) migration and proliferation of endothelial cells, and (3) formation of new vasculature by migrating cells.

Examples of anti-angiogenic agents include, but are not limited to, bevacizumab (AVASTIN®), celecoxib (CELEBREX®), endostatin, thalidomide, EMD121974 (Cilengitide), TNP-470, squalamine, combretastatin A4, interferon-α, anti-VEGF antibody, SU5416, SU6668, PTK787/2K 22584, Marimistal, AG3340, COL-3, Neovastat, and BMS-275291.

Administration

PNA agents in accordance with the invention and pharmaceutical compositions of the present invention may be administered according to any appropriate route and regimen. In some embodiments, a route or regimen is one that has been correlated with a positive therapeutic benefit.

In some embodiments, the exact amount administered may vary from subject to subject, depending on one or more factors as is well known in the medical arts. Such factors may include, for example, one or more of species, age, general condition of the subject, the particular composition to be administered, its mode of administration, its mode of activity, the the severity of disease; the activity of the specific PNA agents employed; the specific pharmaceutical composition administered; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed and the like. Pharmaceutical compositions may be formulated in dosage unit form for ease of administration and uniformity of dosage. It will be understood, however, that the total daily usage of the compositions of the present invention will be decided by an attending physician within the scope of sound medical judgment.

Compositions of the present invention may be administered by any route, as will be appreciated by those skilled in the art. In some embodiments, compositions of the present invention are administered by oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

In some embodiments, PNA agents in accordance with the present invention and/or pharmaceutical compositions thereof may be administered intravenously, for example, by intravenous infusion. In some embodiments, PNA agents in accordance with the present invention and/or pharmaceutical compositions thereof may be administered by intramuscular injection. In some embodiments, PNA agents in accordance with the present invention and/or pharmaceutical compositions thereof may be administered by intratumoural injection. In some embodiments, PNA agents in accordance with the present invention and/or pharmaceutical compositions thereof may be administered by subcutaneous injection. In some embodiments, PNA agents in accordance with the present invention and/or pharmaceutical compositions thereof may be administered via portal vein catheter. However, the invention encompasses the delivery of PNA agents in accordance with the present invention and/or pharmaceutical compositions thereof by any appropriate route taking into consideration likely advances in the sciences of drug delivery.

In some embodiments, PNA agents in accordance with the present invention and/or pharmaceutical compositions thereof may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of subject body weight per day to obtain the desired therapeutic effect. The desired dosage may be delivered more than three times per day, three times per day, two times per day, once per day, every other day, every third day, every week, every two weeks, every three weeks, every four weeks, every two months, every six months, or every twelve months. In some embodiments, the desired dosage may be delivered using multiple administrations (e.g., two, three, four, five, six, seven, eight, nine, ten, eleven, twelve, thirteen, fourteen, or more administrations).

Prophylactic Applications

In some embodiments, PNA agents in accordance with the invention may be utilized for prophylactic applications. In some embodiments, prophylactic applications involve systems and methods for preventing, inhibiting progression of, and/or delaying the onset of cancer or other disorder, and/or any other gene-associated condition in individuals susceptible to and/or displaying symptoms of cancer or other disorder.

Combination Therapy

It will be appreciated that PNA agents and therapeutically active conjugates thereof in accordance with the present invention and/or pharmaceutical compositions thereof can be employed in combination therapies to aid in diagnosis and/or treatment. "In combination" is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

The particular combination of therapies (e.g., therapeutics or procedures) to employ in a combination regimen will take into account compatibility of the desired therapeutics and/or procedures and the desired therapeutic effect to be achieved. It will also be appreciated that pharmaceutical compositions of the PNA agents disclosed herein can be employed in combination therapies (e.g., combination chemotherapeutic therapies), that is, the pharmaceutical compositions can be administered concurrently with, prior to, or subsequent to, one or more other desired therapeutic and/or chemotherapeutic procedures.

PNA agents, or a pharmaceutically acceptable composition thereof, may be administered in combination with chemotherapeutic agents to treat primary or metastatic cancer. In some embodiments, an active ingredient is a chemotherapeutic agent, such as, but not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, methotrexate, actinomycin D, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, imatinib, Gleevec™, sunitinib and Sutent® and combinations thereof.

In some embodiments, PNA agents, conjugates thereof, or a pharmaceutically acceptable composition thereof, are administered in combination with an antiproliferative or chemotherapeutic agent selected from any one or more of Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid.

The particular combination of therapies to employ in a combination regimen will generally take into account compatibility of the desired therapeutics and/or procedures and the desired therapeutic effect to be achieved. It will also be appreciated that the therapies and/or chemotherapeutics employed may achieve a desired effect for the same disorder (for example, an inventive antigen may be administered concurrently with another chemotherapeutic or neurological drug), or they may achieve different effects. It will be appreciated that the therapies employed may achieve a desired effect for the same purpose (for example, PNA agents useful for treating, preventing, and/or delaying the onset of cancer or other disorder may be administered concurrently with another agent useful for treating, preventing, and/or delaying the onset of cancer or disorders), or they may achieve different effects (e.g., control of any adverse effects). The invention encompasses the delivery of pharmaceutical compositions in combination with agents that may improve their bioavailability, reduce and/or modify their metabolism, inhibit their excretion, and/or modify their distribution within the body.

In some embodiments, agents utilized in combination will be utilized at levels that do not exceed the levels at which they are utilized individually. In some embodiments, the levels utilized in combination will be lower than those utilized individually.

In some embodiments, combination therapy may involve administrations of a plurality of PNA agents directed to a single gene. In some embodiments, combination therapy can comprise a plurality of PNA agents that recognize distinct gene sequences.

Kits

The invention provides a variety of kits for conveniently and/or effectively carrying out methods in accordance with the present invention. Kits typically comprise one or more PNA agents.

In some embodiments, kits for use in accordance with the present invention may include one or more reference samples; instructions (e.g., for processing samples, for performing tests, for interpreting results, for administering PNA agents, for storage of PNA agents, etc.); buffers; and/or other reagents necessary for performing tests. In some embodiments kits can comprise panels of PNA agents. Other components of kits may include cells, cell culture media, tissue, and/or tissue culture media.

In some embodiments, kits include a number of unit dosages of a pharmaceutical composition comprising PNA agents. A memory aid may be provided, for example in the form of numbers, letters, and/or other markings and/or with a calendar insert, designating the days/times in the treatment schedule in which dosages can be administered. Placebo dosages, and/or calcium dietary supplements, either in a form similar to or distinct from the dosages of the pharmaceutical compositions, may be included to provide a kit in which a dosage is taken every day.

Kits may comprise one or more vessels or containers so that certain of the individual components or reagents may be separately housed. Kits may comprise a means for enclosing the individual containers in relatively close confinement for commercial sale, e.g., a plastic box, in which instructions, packaging materials such as styrofoam, etc., may be enclosed.

In some embodiments, kits are used in the treatment, diagnosis, and/or prophylaxis of a subject suffering from and/or susceptible to cancer or other disorder. In some embodiments, such kits comprise (i) at least one PNA agent; (ii) a syringe, needle, applicator, etc. for administration of the at least one PNA agent to a subject; and (iii) instructions for use.

These and other aspects of the present invention will be further appreciated upon consideration of the following Examples, which are intended to illustrate certain particular embodiments of the invention but are not intended to limit its scope, as defined by the claims.

EXAMPLES

General Details

Example 1

Inhibition of BRAF Expression using Peptide Nucleic Acids (PNA)

Cell Culture

The present example demonstrates the effect of BRAF mutant specific PNA derivatives cell viability. PNA compounds targeting the BRAF V600E gene mutation were tested against melanoma cell lines that are either BRAF wild type (C918) or BRAF V600E mutant (OCM1A and SK-MEL 7). C918 and OCM1A are uveal melanoma cell lines while SK-MEL 7 is a cutaneous melanoma cell line. C918 was kindly provided by Robert Folberg (University of Illinois, Chicago, Ill.). OCM1A was from Dr. William Harbour (Washington University, St. Louis, Mo.). SK-MEL 7 was from Alan Houghton (Memorial Sloan-Kettering Cancer Center, New York, N.Y.). Cells were cultured in RPMI medium supplemented with 10% FBS, 100 units/mL penicillin, and 100 mg/mL streptomycin and maintained at 37° C. in 5% $CO_2$.

Cell Viability Assays

Figure 2A:
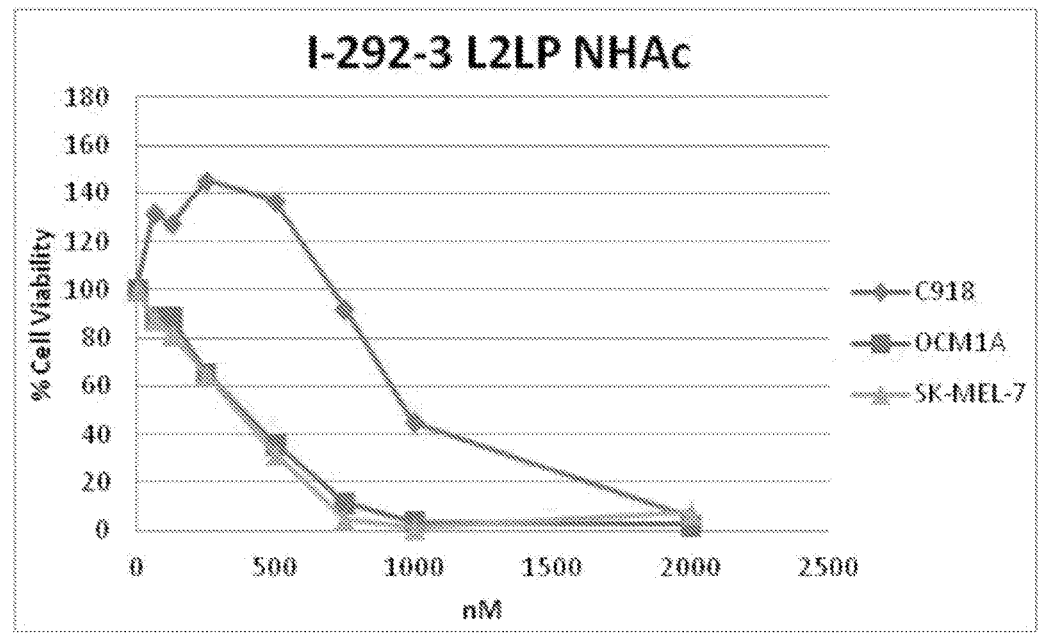
FIG. 2A depicts viability of BRAF V600E mutant (OCM1A, SK-MEL 7) and BRAF wild type (C918) cell lines treated with PNA I-292-3 L2LP NHAc.
Figure 2B:
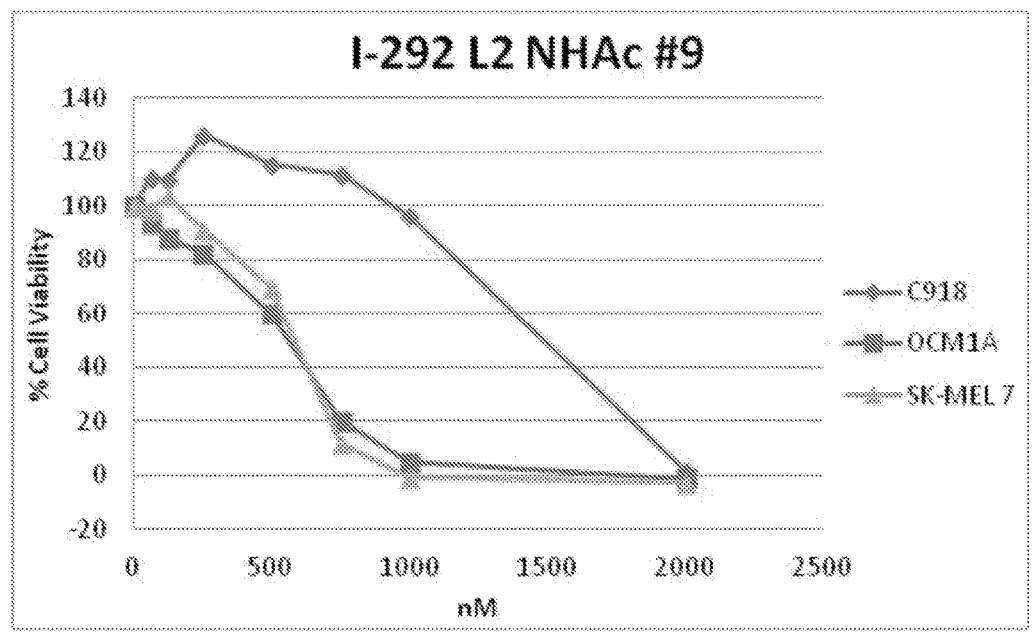
FIG. 2B depicts viability of the same melanoma cell lines treated with PNA I-292-9 L2 NHAc. In both FIGS. 2A and 2B, suppression of cell viability and specificity for cell lines expressing the target mutation was seen in OCM1A and SK-MEL 7 cells treated with the PNA derivatives. Specificity was seen at lower doses in which cell viability of mutant cells is reduced to 20% or less with treatment of PNA derivatives while wild type cell viability (C918) remains at around 100%.

PNA compounds targeting the BRAF V600E gene mutation were tested against melanoma cell lines that are either BRAF wild-type (C918) or BRAF V600E mutant (OCM1A and SK-MEL 7). C918 and OCM1A are uveal melanoma cell lines while SK-MEL 7 is a cutaneous melanoma cell line. Two PNA derivatives in particular, (A) I-292-3 L2LP NHAc and (B) I-292-9 L2 NHAc, showed significant suppression of cell viability and specificity for the cell lines that have the target gene mutation, OCM1A and SK-MEL7. Cells were treated with increasing doses of several PNA derivatives for 72 hours after which the cell viability was measured and calculated relative to the untreated cells. Cells were plated in 96-well plates and treated in triplicates with the indicated concentrations of PNA derivative. Viability was assessed after 72 hours of treatment using the Cell Counting Kit 8 (CCK8) from Dojindo Molecular Technologies according to the manufacturer's instructions. Survival is expressed as a percentage of untreated cells—displaying stagnant uptake <10% ID/g at all timepoints (24-120 hours p.i.), possibly due to enhanced permeation and retention of the tumor's leaky vasculature. As depicted in FIG. 2, cells treated with the PNA derivatives I-292-3 L2LP NHAc (as seen in FIG. 2A) and I-292-9 L2 NHAc (as seen in FIG. 2B) showed significant suppression of cell viability and specificity for the cell lines (OCM1A and SK MEL 7) that have the target gene mutation. The PNA derivative I-292-3 L2LP NHAc inhibited SK MEL 7 cell growth by 100%. The PNA derivative I-292-3 L2LP NHAc inhibited OCM1A cell growth by 96.7%. Incubation of SK MEL 7 and OCM1A cells with I-292-3 L2LP NHAc caused a 62.4% and 40.3% (respectively) decrease in BRAF expression, as determined by Western blot. Specificity is seen at lower doses in which cell viability of mutant cells was reduced to 20% or less with 750 nM treatment of the PNA derivative, while the viability of C918 cells remained around 100%. This demonstrates that the PNA derivatives are effective at suppressing cell viability and are specific for genes with the target BRAF mutation.

Immunoblotting

Cells were treated for 24, 48 and 72-hour treatments with 750 nM PNA and lysed in radioimmunoprecipitation assay (RIPA) buffer supplemented with protease inhibitor cocktail tablets (Roche Diagnostics) and 1 mmol/L Na3VO4. Equal amounts of protein were loaded on 4% to 12% PAGE gels (Invitrogen). Polyvinylidene difluoride (PVDF) membranes were blocked with 5% nonfat dried milk and probed with p-MEK, MEK, p-ERK 1/2 (T202/Y204), ERK 1/2, cleaved PARP, α-tubulin (Cell Signaling Technology), BRAF (Santa Cruz Biotechnology), LC3 (Novus Biologicals) and BRAF V600E (Spring Bioscience).

Figure 3A:
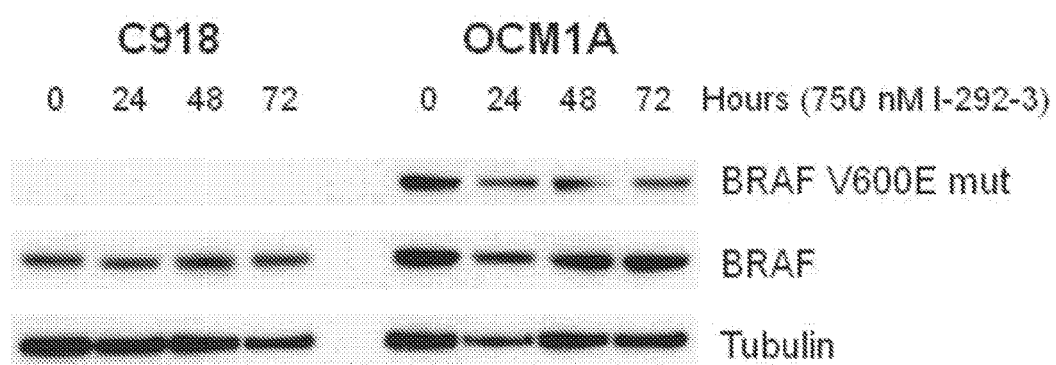
FIG. 3A depicts the extent of mutant and total BRAF protein expression as measured by Western blots in C918 and OCM1A cells. Wild type BRAF was found in both wild type and mutant cell lines, while the BRAF V600E mutant was only found in mutant cells.
Figure 3B:
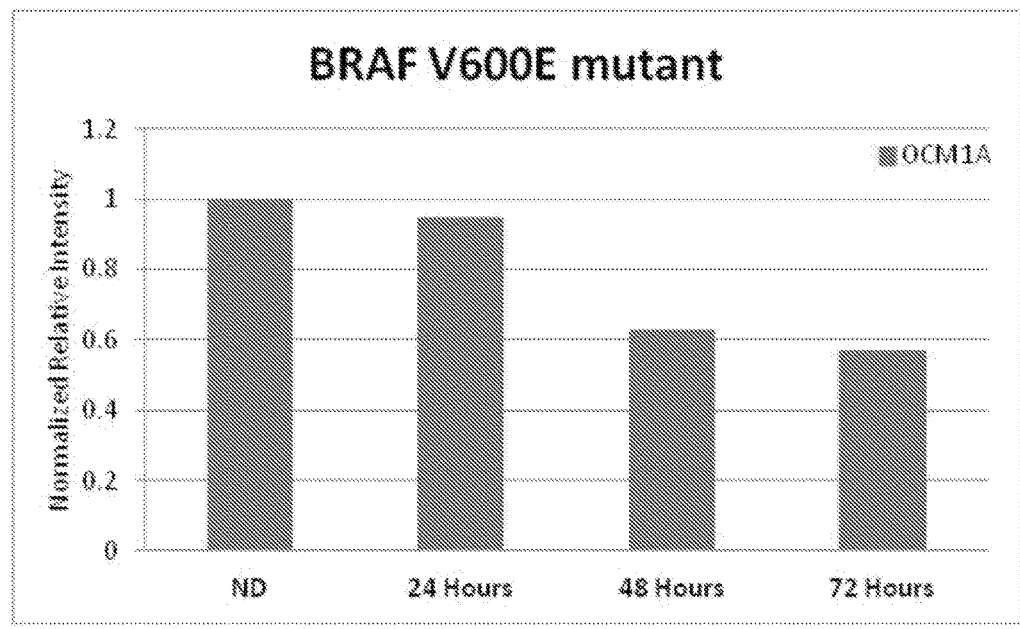
FIG. 3B depicts decreased expression of BRAF V600E mutant protein in OCM1A (BRAF mutant) cell lines over 72 hours of treatment with PNA derivative.
Figure 3C:
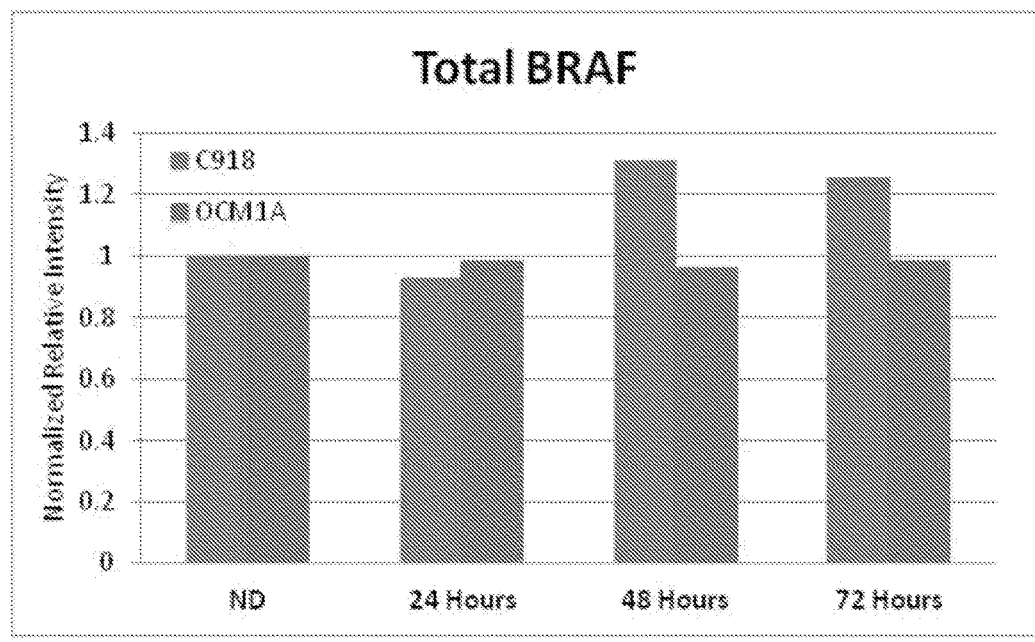
FIG. 3C depicts no significant reduction in total BRAF wild type protein over 72 hours in either OCM1A (mutant) and C918 (wild type) cells treated with I-292-3 L2LP NHAc.

FIG. 3 depicts BRAF mutant and BRAF wild type protein expression in melanoma cells (C918 and OCM1A) treated with 750 nM of the PNA I-292-3 L2LP NHAc for 24, 48 or 72 hours. FIG. 3A depicts the measurement of mutant and total BRAF protein expression as measured by Western blotting in C918 and OCM1A cells. Tubulin expression was also measured as a loading control. Wild type BRAF is found in both wild type and mutant cell lines while the BRAF V600E mutant was only found in mutant cells. Mutant BRAF protein expression is reduced over time in cells treated with the PNA derivative. No mutant BRAF protein was observed in C918 cells as it is a wild-type cell line. FIG. 3B depicts decreased expression of BRAF V600E mutant protein in OCM1A (BRAF mutant) cell lines over 72 hours of treatment with the PNA derivative I-292-3 L2LP NHAc. No mutant BRAF expression was seen in C918 cells. FIG. 3C shows that there was no significant reduction of total BRAF wild type protein over 72 hours in either OCM1A (mutant) and C918 (wild type) cells treated with I-292-3 L2LP NHAc. These results correlate with the specificity and viability suppression seen in the cell viability studies. FIG. 3 demonstrates that PNA derivatives are effective at suppressing cell viability and are specific for genes with the target BRAF mutation. ND=untreated.

Figure 4A:
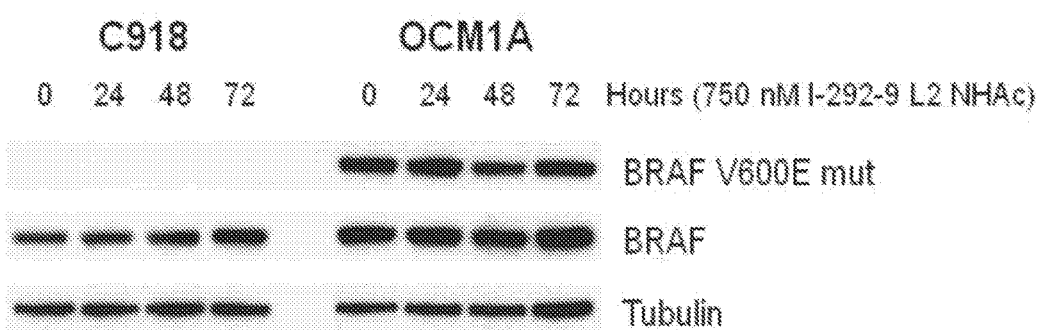
FIG. 4A depicts the extent of mutant and total BRAF protein expression as measured by Western blots in C918 and OCM1A cells. Wild type BRAF was found in both wild type and mutant cell lines, while the BRAF V600E mutant was only found in mutant cells.
Figure 4B:
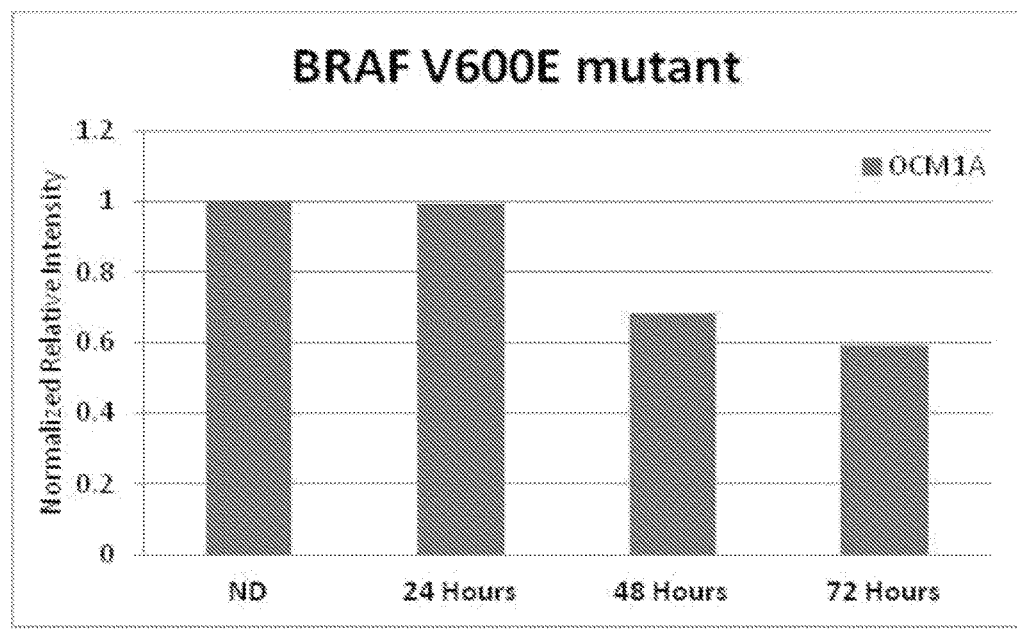
FIG. 4B depicts decreased expression of BRAF V600E mutant protein in OCM1A (BRAF mutant) cell lines over 72 hours of treatment with PNA derivative.
Figure 4C:
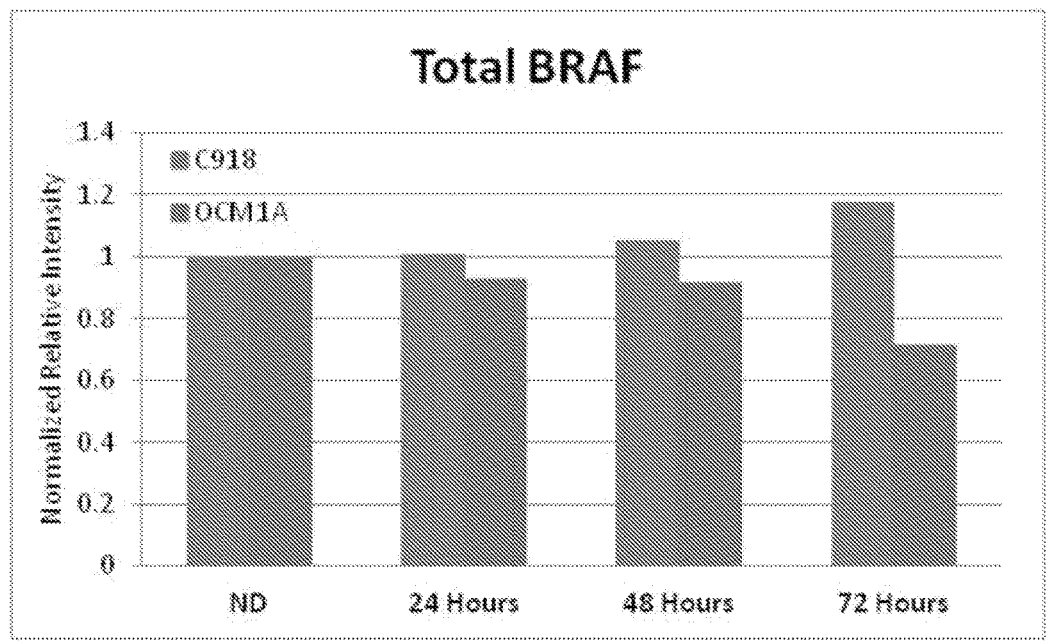
FIG. 4C depicts a slight reduction in total BRAF wild type protein over 72 hours in OCM1A (mutant) cells, but no significant reduction in C918 (wild type) cells treated with I-292-9 L2 NHAc PNA.

FIG. 4 depicts BRAF mutant and BRAF wild type protein expression in melanoma cells (C918 and OCM1A) treated with 750 nM of the PNA I-292-9 L2 NHAc for 24, 48 or 72 hours. FIG. 4A depicts the measurement of mutant and total BRAF protein expression as measured by Western blotting in C918 and OCM1A cells. Tubulin expression was also measured as a loading control. Wild type BRAF is found in both wild type and mutant cell lines while the BRAF V600E mutant is only found in mutant cells. Mutant BRAF protein expression is reduced over time in cells treated with the PNA derivative. No mutant BRAF protein was observed in C918 cells as it is a wild-type cell line. FIG. 4B depicts decreased expression of BRAF V600E mutant protein in OCM1A (BRAF mutant) cell lines over 72 hours of treatment with the PNA derivative I-292-9 L2 NHAc. No mutant BRAF expression was seen in C918 cells. FIG. 4C shows that there was no significant reduction in total BRAF wild type protein over 72 hours in C918 (wild type) cells treated with I-292-9 L2 NHAc. There was a slight decrease of total BRAF protein expression in OC1MA (mutant) cells, but not in C918 (wild type) cells. These results also correlate with the specificity and viability suppression seen in the cell viability studies. FIG. 4 demonstrates that PNA derivatives are effective at suppressing cell viability and are specific for genes with the target BRAF mutation. ND=untreated.

Quantitative Real-Time PCR

Figure 5A:
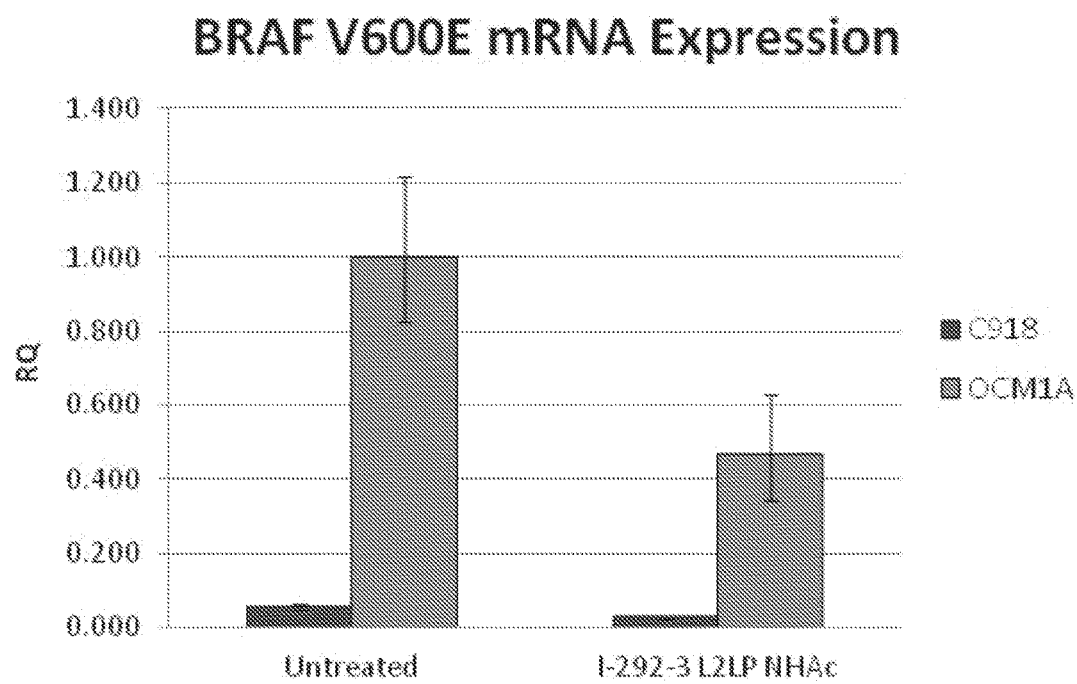
FIG. 5A depicts mutant BRAF V600E mRNA expression quantified by RT-PCR. BRAF V600E mRNA expression was significantly decreased in OCM1A cells when treated with PNA agent I-292-3 L2LP NHAc.
Figure 5B:
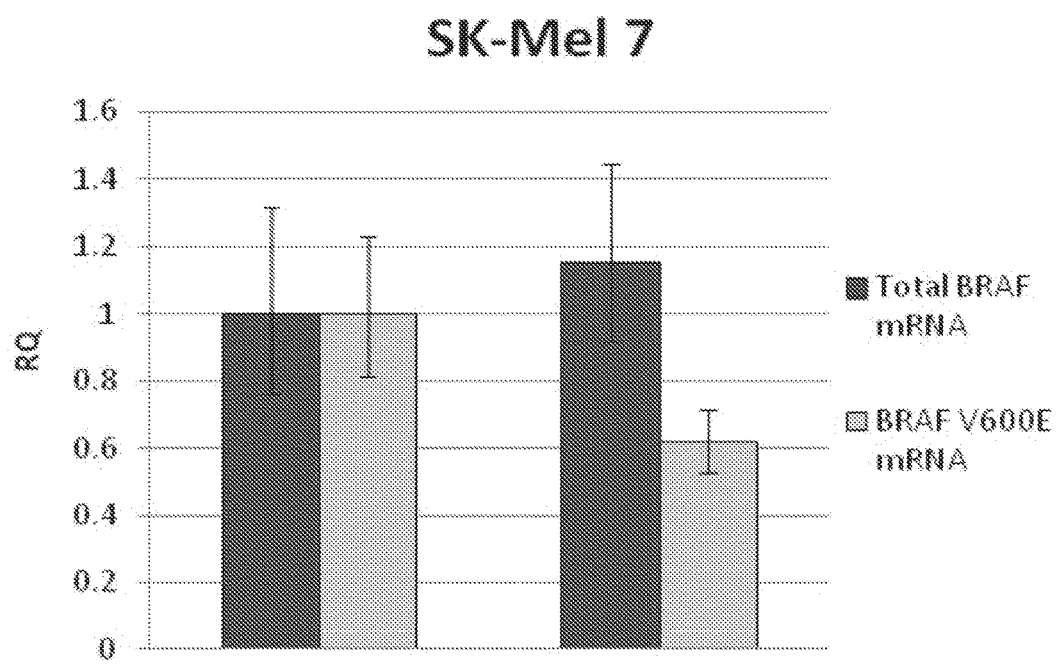
FIG. 5B depicts both BRAF V600E and total BRAF mRNA expression in SK-Mel 7 cells quantified with RT-PCR. In SK-Mel 7 cells, BRAF V600E mRNA expression was decreased significantly after treatment with PNA agent I-292-3 L2LP NHAc. There was no decrease in total BRAF mRNA expression.

C918 and OCM1A cells were treated with 750 nM PNA (I-292-3 L2LP) for 48 hours. Mutant BRAF mRNA expression in cells was quantified using RT-PCT. Specifically, cells were treated and then lysed using TRIzol Reagent® (Invitrogen). Reverse transcription of 1 g of RNA was done using the SuperScript III First-Strand Synthesis System (Invitrogen). Quantitative real-time PCR (qRT-PCR) assays were performed using the 7300 Real Time PCR System (Applied Biosystems). TaqMan gene expression assays, which include gene-specific probe primer sets (Applied Biosystems), were used to detect the indicated genes and glyceraldehyde-3-phosphate dehydrogenase (GAPDH)/hypoxanthine phosphoribosyltransferase (HPRT) mRNA. The relative expression of each gene was calculated by the $\Delta\Delta C_T$ method. See FIG. 5. Cells wild-type for BRAF (C918) as well as mutant cell lines (OCM1A and SK-Mel 7) were treated for 48 hours with 750 nM I-292-3 L2LP NHAc. According to FIG. 5A, $BRAF^{V600E}$ mRNA expression was quantified using RT-PCR. Relative Quantity (RQ) values were normalized with GAPDH loading control and set relative to the mutant BRAF mRNA expression in untreated OCM1A cells (ND). BRAF$^{V600E}$ mRNA expression significantly decreased in OCM1A cells when treated with I-292-3 L2LP NHAc. According to FIG. 5B, Both BRAF$^{V600E}$ and total BRAF mRNA expression in SK-Mel 7 cells were quantified using RT-PCR. RQ values were normalized with GAPDH and set relative to untreated cells. In SK-Mel 7 cells, BRAF$^{V600E}$ mRNA expression also decreased significantly after treatment with I-292-3 L2LP NHAc. There was no observed decrease in total BRAF mRNA expression as a result of treatment. The RT-PCT results for mutant BRAF mRNA expression were consistent with what could be seen in Westerns blots showing decreased protein expression in FIGS. 3 and 4.

Xenograft Mouse Trials

Figure 6A:
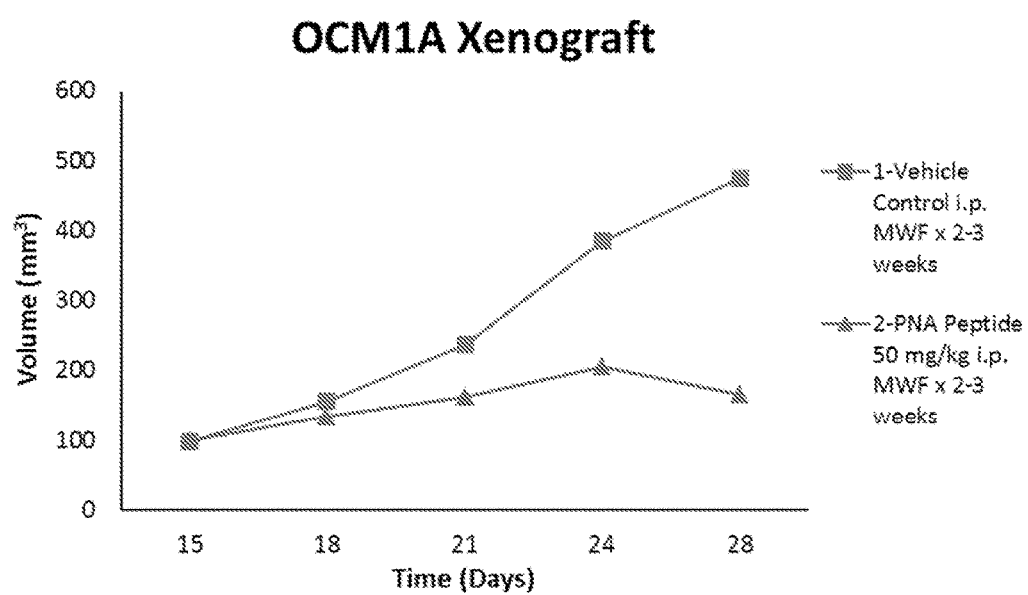
FIG. 6A shows 50% tumor volume regression after three 50 mg/kg IP doses of PNA agent I-292-3 L2LP NHAc given on days 5, 17, 20, and 22. Tumor shrinkage begins to increase more than a week following the last dose.

Athymic mice (3 per group) were inoculated with OCM1A. After 15 days, the size of the developing tumor was sufficient for further measurement and monitoring. The treatment group was given 50 mg/kg dosage of I-292-3 L2LP-NHAc on days 15, 17, 20 and 22. As seen in FIG. 6A, on day 28, the average tumor size was 35% that of the untreated control group. Moreover, one week following the last dose, the average tumor size of the treated group began to shrink by 25% over 4 days.

Figure 6B:
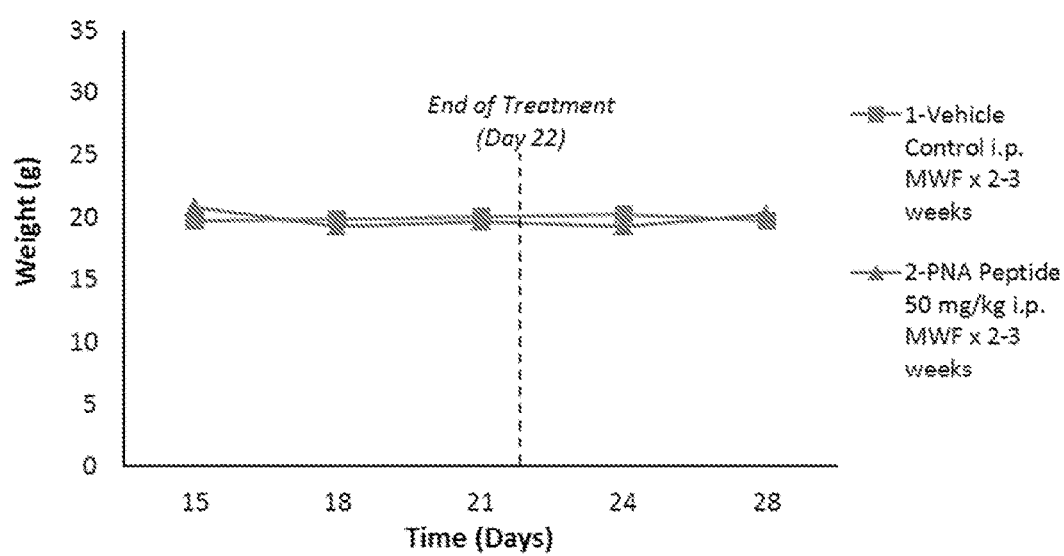
FIG. 6B shows, that treated mice exhibit no side effects as there was no weight loss or changes in daily activity over a the entire length of the treatment shown in FIG. 6A.

Toxicity of the tested PNA derivative was evaluated by measuring weight loss of test animals. At the dosages used, animal weight and activity did not change throughout the 28 day study, as seen in FIG. 6B. These results correlate well with the lack of toxicity observed in previous in vitro studies.

The Memorial Sloan-Kettering Cancer Center Institutional Animal Care and Use Committee and Research Animal Resource Center specifically approved this study. The study also complied with the principles of Laboratory Animal Care (NIH publication no. 85-23, released 1985). All efforts were made to minimize animal suffering.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description. Likewise, those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

In the claims articles such as "a", "an" and "the" may mean one or more than one unless indicated to the contrary or otherwise evident from the context. Thus, for example, reference to "an antibody" includes a plurality of such antibodies, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are presenting, employed in, or otherwise relevant to a given product or process. Furthermore, it is to be understood that the invention encompasses all variations, combinations, and permutations in which one or more limitation, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for anyone of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understand of one of ordinary skill in the art, values that are expressed as ranges can assume any specific value or sub-range within the state ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

What is claimed is:

1. A PNA agent comprising:
   a PNA moiety; and
   a first cationic and hydrophobic peptide at the N-terminus of the PNA moiety, wherein the first peptide comprises lysine residues, and at least one of the lysine residues comprises a palmitoyl side chain moiety; and
   a second cationic and hydrophobic peptide at the C-terminus of the PNA moiety, wherein the second peptide comprises lysine residues, and at least one of the lysine residues comprises a palmitoyl side chain moiety.

2. The PNA agent of claim 1, wherein the first peptide and/or the second peptide consists of lysine residues.

3. The PNA agent of claim 1, wherein the PNA agent has a sequence that has minimal propensity to form hairpin loops.

4. The PNA agent of claim 1, wherein the PNA agent has a sequence that contains less than 60% purines.

5. The PNA agent of claim 1, wherein the PNA moiety has a sequence that targets a gene.

6. The PNA agent of claim 1 wherein the PNA moiety has a sequence that targets a 13-20 nucleotide sequence of a gene with 75% or greater complementarity.

7. The PNA agent of claim 1 wherein the PNA moiety has a sequence that targets a 13-20 nucleotide sequence of a gene with complete complementarity.

8. The PNA agent of claim 5, wherein the gene is an oncogene.

9. The PNA agent of claim 8, wherein the oncogene includes a mutant sequence element and the PNA agent has a sequence that targets a site comprising or consisting of the mutant sequence element.

10. The PNA agent of claim 9, wherein the PNA agent targets a site comprising or consisting of:
    (i) a region of a BRAF oncogene comprising a mutation corresponding to a V600E mutation in a BRAF protein; or
    (ii) a region of a Gnaq gene comprising a mutation corresponding to a Q209L mutation in a Gnaq protein.

11. The PNA agent of claim 8, wherein the PNA agent targets a site comprising or consisting of a region comprising a translocation junction of an oncogene.

12. The PNA agent of claim 11, wherein the PNA agent targets a site comprising or consisting of a region of:
    (i) a MYB-NFIB translocation comprising a junction of MYB and NFIB genes or fragments thereof; or
    (ii) a FUS-CHOP translocation comprising a junction of FUS and CHOP genes or fragments thereof.

13. A pharmaceutical composition comprising the PNA agent of any of claims 1, 2, 3, 4, 5-7, 8-10, 11, and 12 and pharmaceutically acceptable carrier.

* * * * *